United States Patent
Sun

(10) Patent No.: US 8,340,928 B2
(45) Date of Patent: Dec. 25, 2012

(54) SENSOR AND METHOD FOR DETECTING OIL DETERIORATION AND OIL LEVEL

(76) Inventor: Yizhong Sun, Castaic, CA (US)

( * ) Notice: Subject to any disclaimer, the term of this patent is extended or adjusted under 35 U.S.C. 154(b) by 277 days.

(21) Appl. No.: 12/661,779

(22) Filed: Mar. 24, 2010

(65) Prior Publication Data

US 2010/0180663 A1     Jul. 22, 2010

Related U.S. Application Data

(63) Continuation-in-part of application No. 11/899,320, filed on Sep. 5, 2007, now Pat. No. 7,729,870.

(51) Int. Cl.
*G01F 17/00* (2006.01)
*G01F 23/00* (2006.01)
*G01K 13/00* (2006.01)

(52) U.S. Cl. ......... 702/52; 73/53.05; 324/441; 324/698; 702/130

(58) Field of Classification Search ............. 702/50–52, 702/55, 57, 64, 100, 130; 701/29.5, 30; 324/441, 324/698; 340/438, 439, 450.3, 603; 184/103.2; 73/53.05, 61.43

See application file for complete search history.

(56) References Cited

U.S. PATENT DOCUMENTS

| | | | |
|---|---|---|---|
| 4,517,547 A | 5/1985 | Gray et al. |
| 4,646,070 A | 2/1987 | Yasuhara et al. |
| 4,733,556 A | 3/1988 | Meitzler et al. |
| 4,764,258 A | 8/1988 | Kauffman |
| 5,377,531 A | 1/1995 | Gomn |
| 5,540,086 A | 7/1996 | Park et al. |
| 5,929,754 A | 7/1999 | Park et al. |
| 6,014,894 A | 1/2000 | Herron |
| 6,278,281 B1 | 8/2001 | Bauer et al. |
| 6,278,282 B1 | 8/2001 | Marszalek |
| 6,297,733 B1 | 10/2001 | Park |
| 6,535,001 B1 | 3/2003 | Wang |
| 6,577,112 B2 | 6/2003 | Lvovich et al. |
| 6,590,402 B2 | 7/2003 | Wang et al. |
| 6,718,819 B2 | 4/2004 | Schoess |
| 6,917,865 B2 | 7/2005 | Arai et al. |
| 7,143,867 B2 | 12/2006 | Chopra |
| 2006/0114007 A1 | 6/2006 | Cho |
| 2006/0232267 A1 | 10/2006 | Halalay et al. |
| 2009/0063060 A1 | 3/2009 | Sun |

FOREIGN PATENT DOCUMENTS

CN    03140986.5    12/2003

*Primary Examiner* — John H Le

(57) ABSTRACT

A capacitive sensor in its simplest form has three identical plated spatial electrodes, which are positioned equally spaced apart, in order, alignment and parallel with each other. The first and third electrodes are the outer electrodes and connected in parallel by a first lead wire serving as a first electrical pole to be a group of the integrated electrodes. The second electrode is the middle electrode and connected by a second lead wire serving as a second electrical pole. The sensor is applied with an alternating current (AC) excitation signal from an AC device. The present invention method includes application of referencing and sensing capacitive sensors to obtain a measured temperature compensated electrical property of the oil to thereby obtain a measured remaining usage so as to a predicted remaining usage of the oil. Therefore, the top oil level, or the normal, or the abnormal oil deterioration can be concluded according to the measured remaining usage which is respectively larger than, or similar to, or less than the predicted one of the oil.

24 Claims, 11 Drawing Sheets

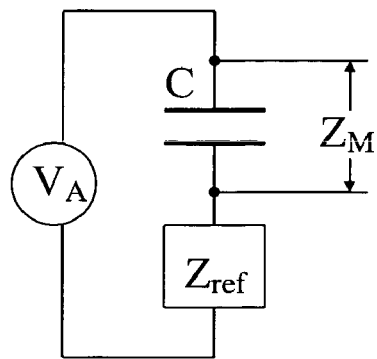
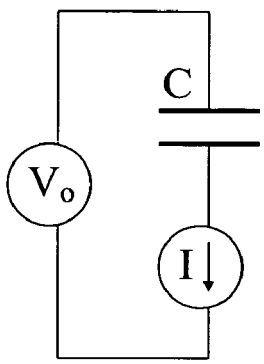
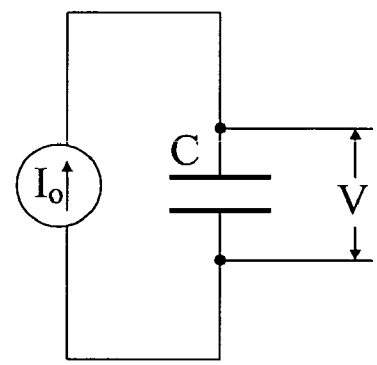
FIG. 5   FIG. 6   FIG. 7
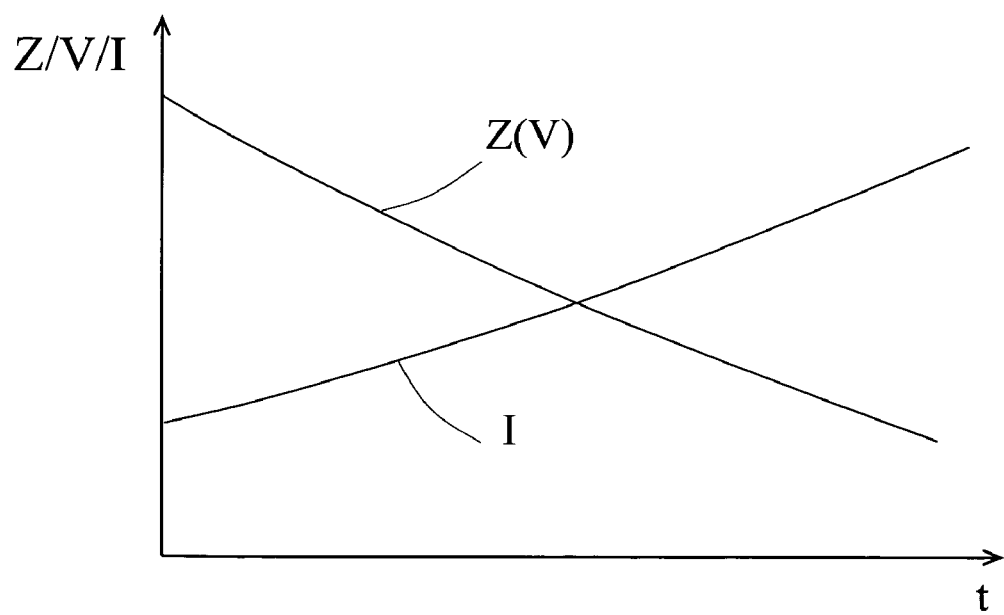
FIG. 8

SENSOR AND METHOD FOR DETECTING OIL DETERIORATION AND OIL LEVEL

CROSS-REFERENCE TO RELATED APPLICATIONS

This application is a continuation-in-part of U.S. patent application Ser. No. 11/899,320 filed on Sep. 5, 2007, now U.S. Pat. No. 7,729,870.

BACKGROUND OF THE INVENTION

1. Field of the Invention

The present invention is generally related to oil which is used in machinery such as internal combustion engines and electrical transformers, and more particularly related to sensor and method for the on-line detection of the oil level, and the oil deterioration which occurs in the presence or absence of water.

2. Description of the Prior Art

Sensors and methods for detecting oil deterioration and oil level are well known. The following 21 patents and published patent applications are the closest prior art references which are related to the present invention.

1. U.S. Pat. No. 4,517,547 issued to Gary et al. on May 14, 1985 for "Water-In-Fuel Sensor Circuit And Method" (hereafter the "Gary Patent");
2. U.S. Pat. No. 4,646,070 issued to Yasuhara et al. on Feb. 24, 1987 for "Oil Deterioration Detector Method And Apparatus" (hereafter the "Yasuhara Patent");
3. U.S. Pat. No. 4,764,258 issued to Kauffman on Aug. 16, 1988 for "Method For Evaluating The Remaining Useful Life Of A Hydrocarbon Oil" (hereafter the "Kauffman Patent");
4. U.S. Pat. No. 5,540,086 issued to Park et al. on Jul. 30, 1996 for "Oil Deterioration Sensor" (hereafter the "Park First Patent");
5. U.S. Pat. No. 5,929,754 issued to Park, et al. on Jul. 27, 1999 for "High Sensitivity Capacitive Oil Deterioration and Level Sensor" (hereafter the "Park Second Patent");
6. U.S. Pat. No. 6,297,733 issued to Park, et al. on Oct. 2, 2001 for "Stable, Reliable Capacitive Oil Deterioration And Level Sensor" (hereafter the "Park Third Patent");
7. U.S. Pat. No. 5,377,531 issued to Gomn on Jan. 3, 1995 for "Portable Oil Change Analyzer" (hereafter the "Gomn Patent");
8. U.S. Pat. No. 4,733,556 issued to Meitzler et al. on Mar. 29, 1988 for "Method And Apparatus For Sensing The Condition of Lubricating Oil In An Internal Combustion Engine" (hereafter the "Meitzler Patent");
9. U.S. Pat. No. 6,278,282 issued to Marszalek on Aug. 21, 2001 for "Method And System For Determining Oil Quality" (hereafter the "Marszalek Patent");
10. U.S. Pat. No. 6,590,402 issued to Wang et al. on Jul. 8, 2003 for "Engine Oil Condition Sensor" (hereafter the "Wang First Patent");
11. U.S. Pat. No. 6,535,001 issued to Wang on Mar. 18, 2003 for "Method and device For Sensing Oil Condition" (hereafter the "Wang Second Patent");
12. U.S. Pat. No. 6,577,112 issued to Lvovich et al. on Jun. 10, 2003 for "Method And Apparatus For On-Line Monitoring Of Quality And/Or Condition of High Resistive Fluids" (hereafter the "Lvovich Patent");
13. U.S. Pat. No. 7,143,867 issued to Chopra on Dec. 5, 2006 for "Electronic Oil Level Detection And Replacement System" (hereafter the "Chopra Patent");
14. United States Patent Application Publication No. 2006/0232267 issued to Halalay et al. on Oct. 19, 2006 for "Determining Quality Of Lubricating Oils In Use" (hereafter the "Halalay Publication");
15. U.S. Pat. No. 6,718,819 issued to Schoess on Apr. 13, 2004 for "Oil Quality Sensor System, Method and Appatus" (hereafter the "Schoess Patent");
16. U.S. Pat. No. 6,278,281 issued to Bauer et al. on Aug. 21, 2001 for "Fluid Condition Monitor" (hereafter the "Bauer Patent");
17. U.S. Pat. No. 6,014,894 issued to Herron on Jan. 18, 2000 for "Motor Sensor System" (hereafter the "Herron Patent");
18. U.S. Pat. No. 6,917,865 issued to Arai et al. on Jul. 12, 2005 for "Engine Oil, Degradation-Determining System And Method, And Engine Control Unit" (hereafter the "Arai Patent");
19. United States Patent Application Publication No.: 2006/0114007 issued to Cho on Jun. 1, 2006 for "Apparatus, A method, And Measuring Sensors For Scanning States Of Engine Oil" (hereafter the "Cho Publication");
20. China Patent No.: 03140986.5 issued to Sun on Dec. 3, 2003 for "Methods For Detecting Deterioration In Oil" (hereafter the "Sun Patent"); and
21. United States Patent Application Publication No.: 2009/0063060 issued to Sun on Mar. 5, 2009 for "Methods for Detecting Oil Deterioration and Oil Level" (hereafter the "Sun Publication").

The Gary Patent discloses an invention of a water-in-fuel sensor circuit and method. The invention includes a reference capacitor coupled in parallel with a variable capacitor which is immersed in a fuel of a fuel tank, wherein two capacitors are alternately charged and discharged by an oscillator. Water in the fuel will cause increase of the effective capacitance value of the variable capacitor which reduces the absolute magnitude of the current that is detected. The absolute magnitude of the detected current can be utilized to indicate excessive water levels in the fuel.

The Yasuhara Patent illustrates an oil deterioration sensor and method. The oil deterioration sensor is comprised of a voltage divider which is constructed by a sensor capacitor and a fixed capacitor, wherein a constant frequency AC voltage source is applied to the voltage divider. Therefore a developed voltage across the sensor capacitor corresponds to the dielectric constant of the lubrication oil, from which the oil deterioration can be detected. The frequency of the AC voltage ranges from 50 KHz to 500 KHz.

The Kauffman Patent discloses a method for evaluating a remaining useful life of a hydrocarbon oil containing at least one additive species. A voltammetric analysis is applied to test a remaining amount of the additive, which results in an amount of the redox current corresponding to the remaining amount of the additive. Therefore, the remaining useful life can be concluded in accordance with the magnitude of the current.

The Park First Patent discloses an oil deterioration sensor. The sensor includes an oil deterioration sensor capacitor which is constructed with two metal plates, and a total reference capacitor which includes an external fixed reference capacitor. The capacitances of the respective oil deterioration capacitor and total reference capacitor provide an engine oil deterioration indication for the oil deposited within a gap of the metal plates. The oil deterioration sensor further includes a temperature sensitive resistor thermally connected to a substrate of the sensor for providing a temperature adjustment to the engine oil deterioration indication, and a circuitry utilizing the capacitances of the respective oil deterioration sensor capacitor and total reference capacitor to generate the engine oil deterioration indication.

The Park Second Patent discloses a combination of a capacitive oil deterioration and oil level sensor. The sensor comprises a conductive cylindrical housing member that includes a conductive shielding member defining a ground electrode, and a conductive inner member defining a measuring electrode. The sensor also includes electronics adapted to generate signals indicative to the deterioration of the oil deposited within a gap of two electrodes and a level of the oil along the length of the cylindrically shaped sensor. The oil level is monitored from detecting a ratio of the capacitance of oil dielectric constant over the capacitance of the oil level as $C_\in/C_L$.

The Park third Patent discloses a sensor which has a similar main structure as the sensor of the Park Second Patent. In addition, the patented sensor applies electronics including at least one isolating capacitor to eliminate a flow of current between two electrodes that may cause a build up of an unwanted material on the two electrodes that define the capacitor. This build up of the unwanted material may cause an undesirable effect in the sensor output signal. The Park Third Patent further discloses the capacitance $C_\in$ of the oil deterioration and level sensor capacitor is proportional to $\in$ times L, where $\in$ is the dielectric constant of the oil and L is the length of the inner electrode. Therefor, the oil level affects the length of the inner electrode, which also affects the capacitance of the sensor.

The Gomm Patent discloses a portable oil change analyzer for a laboratory oil test, which is comprised of a viscosity analyzer and a contamination analyzer. The contamination analyzer is based on an optical mechanism, where increase of contaminates in oil results in decrease of a light intensity for an incident light after passing through the oil sample. The oil quality is determined by results from both viscosity and contamination tests.

The Meitzler Patent discloses an oil deterioration sensing system comprising an identical reference capacitor and sampling capacitor immersed in the respective fresh oil and sample oil under test. The system tests change of responded frequencies of the tested oil when both capacitors are under excitation of applied frequencies. Results of the test indicates change of the responded frequencies is consistent with change of the viscosity of the oil which is related to the aging of the oil.

The Marszalek Patent discloses a method for detecting quality of lubricating oil, which includes a sensor having two electrodes. The method includes applying a potential of a first amplitude to the electrodes immersed in an oil in use, testing a first voltage phase lag, increasing amplitude of the potential to a second amplitude, testing a second voltage phase lag. Therefor, the patented invention can determine the quality of the oil based on the voltage phase lags.

The Wang First Patent discloses a method of detecting engine oil if it is contaminated by presence of antifreeze. The method includes applying a series of different voltages to a sensor immersed in an oil in use, testing a corresponding series of the current sensor output voltages, determining a voltage difference between each of the current sensor output voltage relative to a reference voltage, thereby determining if presenting the antifreeze in the oil after comparing the voltage differences.

The Wang Second Patent discloses a device for testing oil condition including an oil condition sensor having electrodes. The electrodes are separated by a gap that is filled with an engine oil. A processor connected to the sensor can be used to determine if the oil is at a first, second and third stage of oil degradation, which is corresponding to a first, second and third sensor output signal trend.

The Lvovich Patent discloses an apparatus and a method for monitoring a highly electrically resistive fluid. The method includes applying an AC signal that comprises at least two different AC electrical potentials, with at least one AC potential having a none-zero DC offset, measuring the fluid's electrical response including impedance and its real and imaginary components, thereby determining the fluid quality.

The Chopra Patent discloses an invention of electronic oil level and replacement system. The invention is based on the physical phenomenon that a position of a float member is dependent upon a level of the oil. Therefore, a change of the vertical position of the float member will cause a motion of a piston which opens or stops a passage to an oil reservoir. Therefore, the replacement system can work. Following the same mechanism, another float member can activate a lower oil level electric switch or an upper oil level electric switch according to the respective oil level, so that the oil level can be electrically detected.

The Halalay Patent illustrates a method to detect a change of oil resistivity over a period of elapsed times for an oil in use, which is consistent with to a change of the oil viscosity over the time. Therefore, the method can be applied to monitor oil deterioration including a remaining useful life of the oil.

The Schoess Patent discloses an apparatus for determining condition of the engine lubricating oil. The apparatus includes a sensor have a plurality of spaced apart electrode pairs on a nonconductive polymer film. A forcing-function waveform reactive circuit is applied to the sensor input electrode as a common voltage potential. The output current of the sensor output electrode is converted to an equivalent voltage. Based on the voltage values, the sensing apparatus will determine the oil's condition, and will therefore trigger a trouble code if the equivalent voltage falls within a predetermined range.

The Bauer Patent discloses a fluid condition monitor, comprising a capacitive spaced array electrode probe which is immersed in the fluid and is applied by an oscillating voltage. A first frequency of at least one hertz is applied and a corresponding first current of the electrode probe is measured. A second frequency is then applied and a corresponding second current is measured. Therefore a difference between the first and second current can be obtained, which can be used to predicate the fluid condition, as compared with a predetermined threshold value.

The Herron Patent discloses a motor sensor system for detecting the presence of water in a sealed oil chamber of an engine. The sensor system includes a plurality of flat conductive and insulative annular rings which are alternatively sandwiched together to be an assembly. The assembly is mounted on the propeller shaft in the sealed oil chamber of an engine. Each conductive ring is connected to a remote alarm circuit. In addition, the ring includes a plurality of radially inwardly extending probe sections which are circumferentially spaced around the propeller shift. Thus, if water enters the engine in running, a mixture of the oil and water spans one or more of the gaps formed between the complementary probe sections of the conductive element. Therefore, it completes the alarm circuit and provides an operator of the engine a warning of the water in the oil of the engine.

The Arai Patent discloses an engine oil degradation-determining system. The system applies a crankshaft angle sensor which detects the engine rotation speed of an internal combustion engine. Therefore, an electronic device calculates a cumulative revolution number indicative of a degradation degree of the engine oil. An oil level sensor detects an oil level of the engine oil, which is comprised of an upper limit switch and a lower limit switch. Basically, the upper switch monitors the oil level when it reaches a predetermined upper limit, and the lower limit switch monitors the oil level when it reaches a predetermined lower limit. Following this detection mechanism, the invention of the oil level sensor enables to monitor the oil level.

The Cho Patent Application Publication relates to an apparatus, a method, and measuring sensors for scanning engine oil of a vehicle. The invention includes a viscosity sensor which predominantly monitors the oil deterioration, and an oil level sensor which monitors the oil level. The oil level sensor in FIG. 8 has an input electrode 106 having a shape of a pipe and is installed to have an electric current applied thereto, and an oil level electrode 105 having a shape of a pipe installed apart from an inner surface of the input electrode 106 so as to receive the electric current from the input electrode 106. Therefore, the oil level is calculated on the basis of the capacitance and dielectric constant measured between the oil level electrode 105 and input electrode 106.

The Sun Patent discloses methods for detecting deterioration in oil, comprising a preferred dual sensor having reference and sensing capacitors. Therefore, variations of electrical properties of the sensing capacitor disposed in the oil, which are caused by the temperature variations of the oil, can be compensated by the same variations of electrical properties of the reference capacitor. This results in a temperature compensated electrical property of the sensing capacitor, which represents the oil deterioration. Following this concept, it can establish a profile of predicted temperature compensated electrical properties for the oil, which includes the properties of the respective new oil and spent oil. The profile corresponds to a range of usages from the respective new and spent oil. Therefore, a remaining usage ratio R of the oil can be calculated according to the obtained temperature compensated electrical property, which further determines a remaining usage of the oil as the remaining usage ratio times the range of usages. In addition, various methods are disclosed to detect presence of water in oil.

The Sun Publication discloses methods for detecting oil conditions including a top level of an oil in an oil system which is reduced to a top level of a threshold amount of the oil, a normal oil deterioration which occurs in the absence of water and has a confirmed remaining usage of the oil, and an abnormal oil deterioration which occurs in the presence of water. The methods include a first preferred embodiment which applies reference and sensing capacitors to obtain a measured temperature compensated electrical property of the oil. From which a quantitatively measured remaining usage is obtained so as to a predicted one for the oil. Therefore, the top oil level, or the normal or the abnormal oil deterioration can be concluded according to the measured remaining usage which is respectively larger than, or similar to, or less than the predicted one for the oil. A second preferred embodiment only includes the sensing capacitor for obtaining the measured temperature compensated electrical property of the oil. Variations to the embodiments lead to application of at least two sensing capacitors to monitor an uneven distribution of the oil deterioration or a full range of the level of the oil in the entire oil system.

It will be appreciated that the Sun Patent and Publication disclose unique methods, which apply a measurement sensor including a capacitor operated by an AC voltage for monitoring oil condition including deterioration and level of an oil in use. However, there is still a room for improving the conventional capacitor having two plates regarding its electrical characteristics, and output that is fundamental of the detection technology. This is because the output of the capacitor is limited by the gap between the two plates, which are electrically polarized according to the alternative polarities of the applied AC excitation. Therefore, the two plates alternatively having different electrical polarities are exposed to an electrical environment that surrounds the capacitor, so that there is a great chance for a cross talk between the capacitor and surrounding electrical environment if the capacitor is not electrically shielded.

There is a significant need to have a method and a sensor having improved output and electrical characteristics for detecting oil conditions including a top level of an oil system which is reduced to a top level of a threshold amount of the oil, and oil deterioration which occurs in the absence or presence of water, to significantly improve usage of the oil and protect machines which are lubricated by the oil.

SUMMARY OF THE INVENTION

The objects of the present invention sensor and method are directed to detect oil conditions including oil deterioration, oil level and a remaining usage of an oil. The oil deterioration can be occasioned by factors such as the thermo-oxidative breakdown, additive depletion, water contamination, breakdown product polymerization, and carbon particulates which are produced in the combustion process. During its deterioration, the oil in use is usually consumed so that a top level of the oil is reduced. These conditions are critical for maintaining, thus protecting a machine which uses the oil, such as internal combustion engines and electrical transformers.

The present invention sensor comprises a measurement sensor including a general embodiment of a sensing capacitive sensor operated by an alternating current (AC) including periodic electrical excitation signal at a frequency from an AC device for detecting deterioration and level of the oil in use. The embodiment applies a total of an odd number of identical plated spatial electrodes, which are positioned equally spaced apart, in order, alignment and parallel with each other. Within the electrodes, the even numbered electrodes are electrically connected in parallel by a first lead wire serving as a first electrical pole to thereby form a first group of the integrated electrodes. The odd numbered electrodes are electrically connected in parallel by a second lead wire serving as a second electrical pole to thereby form a second group of the integrated electrodes. The present invention sensing capacitive sensor possesses properties of high output, reduced physical size and improved electrical characteristics.

In a preferred embodiment of the present invention sensing capacitive sensor in its simplest form, the sensor has first, second and third identical plated spatial electrodes, which are positioned to be equally spaced apart, in order, alignment and parallel with each other. The first and third plated electrodes are the outer electrodes and connected in parallel by a first lead wire serving as a first electrical pole to be a group of the integrated electrodes. The second plated spatial electrode is the middle electrode and connected by a second lead wire serving as a second electrical pole. In operation, the AC device is connected to the first and second electrical poles of the sensing capacitive sensor.

The preferred embodiment sensor of the present invention has a number of advantages. First, the two outer electrodes have the same electrical polarity when an AC voltage is applied to the sensing capacitive sensor. Therefore, the outer electrodes shield the middle electrode having the opposite electrical polarity. This makes the sensing capacitive sensor have a symmetric electrical field relative to an external electromagnetic environment, which is critical to its performance since the sensor that is operated by the AC electricity is surrounded by the external electromagnetic environment.

Second, as compared with four plates of two prior art capacitors connected in parallel, the present invention sensing capacitive sensor has three plated electrodes and the same output if the physical parameters of the first and second plated electrodes are the same as those of two plates of one prior capacitor. However, the present invention sensor is less one electrode to thereby have a reduced size. This structural characteristics is important for designing a miniaturized sensor, therefore, the present invention has the advantage in the reduced sizes while keeping the same electrical output.

The present invention method includes a first embodiment of applying a dual sensor configuration that has identical measurement and reference sensors including the respective sensing and referencing capacitive sensors. The sensing capacitive sensor of the measurement sensor is immersed in the oil in use and positioned to align with a level of a predetermined threshold amount of the oil. Therefore, the oil deterioration or top level of the predetermined threshold amount of the oil can be determined from measuring one of various electrical properties of the respective sensing and referencing capacitive sensors.

In a situation during the oil deterioration when an amount of the oil is not significantly reduced so that the sensing capacitive sensor is still fully immersed in the oil, the electrical property of the sensor is influenced by increase of the dielectric constant of the oil due to aggravation of the oil deterioration, or by significant increase of the dielectric constant due to presence of water in the oil. In another situation when an amount of the oil is significantly reduced to the predetermined threshold amount, it causes to lower a height of a top level of the oil, which is insufficient for the sensing capacitive sensor to be fully immersed in the oil. Therefore, the sensor is partially filled with the air. According to this condition, the electrical property of the sensor is predominantly influenced by the dielectric constant of the air which is substantially smaller than the dielectric constant of the oil.

In accordance with a first preferred embodiment of the present invention method, the reference sensor including the referencing capacitive sensor is also used in addition to the measurement sensor. The referencing capacitive sensor is immersed in a reference oil including a dry new oil or a dry spent oil or a dry partially spent oil having the same thermal properties as those of the oil in use. The reference oil and oil in use are placed in the same temperature environment. In the first preferred embodiment method, the electrical properties of the respective sensing and referencing capacitive sensors are combined to thereby eliminate fluctuations of the measured electrical properties of the sensing capacitive sensor, where the fluctuations are induced by variations of the oil temperature. Therefore, from a first measurement the preferred embodiment of the present invention method enables to obtain a first measured temperature compensated electrical property of the sensing capacitive sensor, which represents a first measured temperature compensated electrical property of the oil that is known not to contain water.

In this manner, a predicted temperature compensated electrical property profile for the oil also can be simulated, which correlates to a full range of actual usages of the oil to thereby represent an entire deterioration of the oil when it is dry. Within the profile, it can determine a first predicted temperature compensated electrical property of the oil as compared with the first measured temperature compensated electrical property, wherein they are correlated to a same first actual usage of the oil.

Applying the measured temperature compensated electrical property, a measured remaining usage of the oil can be obtained from the present invention, so as to a predicted remaining usage of the oil according to the predicted temperature compensated electrical property.

Following the first measurement, the present invention method applies a second measurement according to the same first actual usage of the oil, which obtains a second measured temperature compensated electrical property so as to a second measured remaining usage of the oil. Comparing the first predicted remaining usage of the oil with the second measured remaining usage, a normal oil deterioration, the oil deterioration which occurs in the absence of the water contamination between two measurements, can be concluded if the second measured remaining usage of the oil is similar to the first predicted remaining usage. Therefore, the second measured remaining usage of the oil can be confirmed as a remaining actual usage, which is useful for a user of the machine to set a schedule of the oil change.

If the second measured remaining usage of the oil is apparently smaller than the first predicted remaining usage, an abnormal oil deterioration, the oil deterioration which occurs in the presence of the water contamination, can be concluded. This conclusion is based on a fact that the dielectric constant of water is substantially larger than the dielectric constant of the oil, which causes that the measured temperature compensated electrical property of the sensing capacitive sensor filled with the mixture of the oil and water is different from the predicted electrical property of the same sensor fully filled with the oil. The difference further leads to a false phenomenon of the smaller measured remaining usage for the oil mixed with water.

If the second measured remaining usage of the oil is noticeably larger than the first predicted remaining usage, it can conclude that a top level of the oil is reduced to the top level of a predetermined threshold amount of the oil. In this situation, the sensing capacitive sensor which is positioned to align with the top level of the threshold amount of the oil is partially filled with air. Since the dielectric constant of the air is substantially smaller than the oil dielectric constant, the measured property of the sensing capacitive sensor partially filled with the air is different from the predicted property of the same sensor fully filled with the oil. The difference further leads to a false phenomenon of the larger measured remaining usage of the oil.

Obtaining the above illustrated abnormal oil conditions, the user of the machine can take appropriate actions to protect the machine from damage.

Besides of applying the second remaining usage of the oil, the first preferred embodiment of the present invention method also can conclude that water is likely to be present in the oil in application of the second measured temperature compensated electrical property.

The present invention sensor also discloses variations of the sensor embodiment, which comprise at least two measurement sensors including the respective at least two sensing capacitive sensors. The at least two measurement sensors can be placed to different locations of an oil system of the machine so that the user of the machine can determine if there is an uneven distribution of the oil deterioration through the entire oil system. This information is particularly useful for a large internal combustion engine such as one equipped in a locomotive or ship, where water can exist in particular locations of the oil system of the engine.

If the at least two measurement sensor can be positioned along a vertical orientation, a change of a full range of the oil level can be monitored when the oil is gradually consumed so as to gradually lower the top oil level. Accordingly, each of the at least two sensing capacitive sensors will be changed sequentially from a sensor filled with the oil to one filled with air so as to a sequential change of the electrical properties of each of the at least two sensors. Therefore, an in situ oil top level can be monitored from detecting such sequential change of the electrical properties of the respective at least two sensing capacitive sensors.

In accordance with a second preferred embodiment method, the present invention only applies the measurement sensor. A measured temperature compensated electrical property profile of the sensing capacitive sensor can be obtained so as to a predicted property profile according to a number of known temperature compensation methods. Under this situation, the second embodiment further enables to derive the second measured remaining usage of the oil. Therefore, the second embodiment of the present invention can determine oil conditions including a top oil level which is reduced to the top level of the predetermined threshold amount of the oil during the oil reduction process, the abnormal oil deterioration and normal oil deterioration including a confirmed remaining usage of the oil, following the same strategy of comparing the second measured remaining usage with the first predicted one. In addition, the second embodiment further enables to apply at least two measurement sensor including the respective sensing capacitive sensors for monitoring if there is an uneven distribution of the oil deterioration or a change of a full range of the oil level of the oil system in the machine.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 5 is a circuit diagram showing an impedance measurement using a voltage divider;

FIG. 6 is a circuit diagram showing a current measurement using a constant voltage source;

FIG. 7 is a circuit diagram showing a voltage measurement using a constant current source;

FIG. 8 is a graph showing profiles of the respective impedance Z, voltage V, and current I for an oil which deteriorates over the time;

In FIG. 16 the independent variable is presented as the time t;

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Oil conditions are critical for maintaining, thus protecting a machine which uses an oil. The conditions include abnormal deterioration of the oil which occurs in the presence of water, or normal deterioration of the oil which occurs in the absence of water and contains a remaining usage of the oil which is useful for a schedule to change the oil, and a top level of the oil in the machine when it is reduced to a top level of a threshold amount of the oil. The present invention sensor and method is aimed to detect these conditions from applying an improved capacitive sensor having improved electrical output and characteristics, thereby providing respective indications to a user of the machine for taking appropriate actions to protect the machine from damage, and is disclosed in the following two sections.

I. Sensor and Method for Detecting Deterioration of an Oil

In a machine such as an internal combustion engine, lubricating oil is used to reduce friction between moving parts of an engine. Over time however the oil deteriorates and is therefore less effective in protecting the engine from damage. The life span of the oil is limited by factors such as the thermo-oxidative breakdown, additive depletion, water contamination, breakdown product polymerization, and carbon particulates which are produced in combustion of the engine operation.

Figure 1:
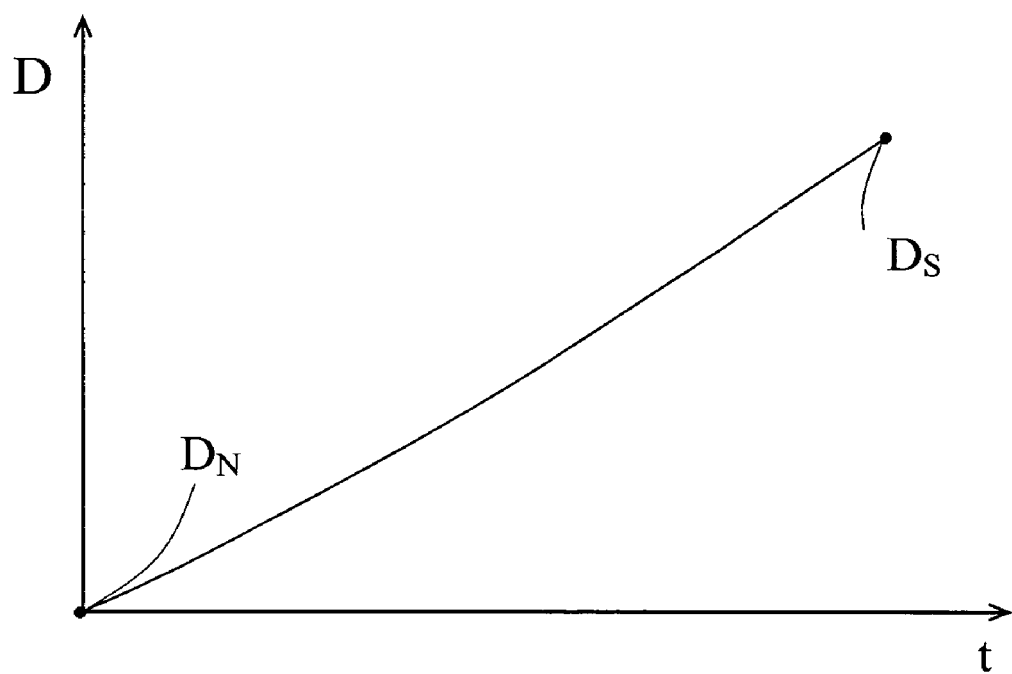
FIG. 1 is a graph showing deterioration of an oil in use as the function of time.

Within the above mentioned facts, the water contamination effects differently, as compared with the rest of facts to effect the oil chemical, physical and electrical properties. Therefore, it will be appreciated that oil deterioration can be classified as the normal one which occurs in the absence of water and the abnormal one which occurs in the presence of water. FIG. 1 shows a normal oil deterioration profile D according to the elapsed times t. When an oil is new or unused there is no deterioration, which is shown at a point "$D_N$". As time progresses and the oil is used, contaminants build up. Eventually, the deterioration reaches a point "$D_S$" when the oil is spent and should be changed.

Similarly, the oil used in power transformers is subject to breakdown. Primary causes for deterioration include heat, oxygen, moisture, and electrical stress: partial discharge and arcing.

It is well known that the dielectric constant of the oil increases with increase of the oil contamination and thus deterioration. Therefore, by making use of this property, a degree of the oil deterioration may be measured electrically. This can be done by placing a sensor such as a capacitive probe in the oil and measuring the electrical properties of the oil as manifested by electrical properties of the probe. As contaminants build up the deterioration correspondingly aggravates and the dielectric constant $\in$ of the oil increases thereby increasing the probe's capacitance $C_p$.

Figure 2:
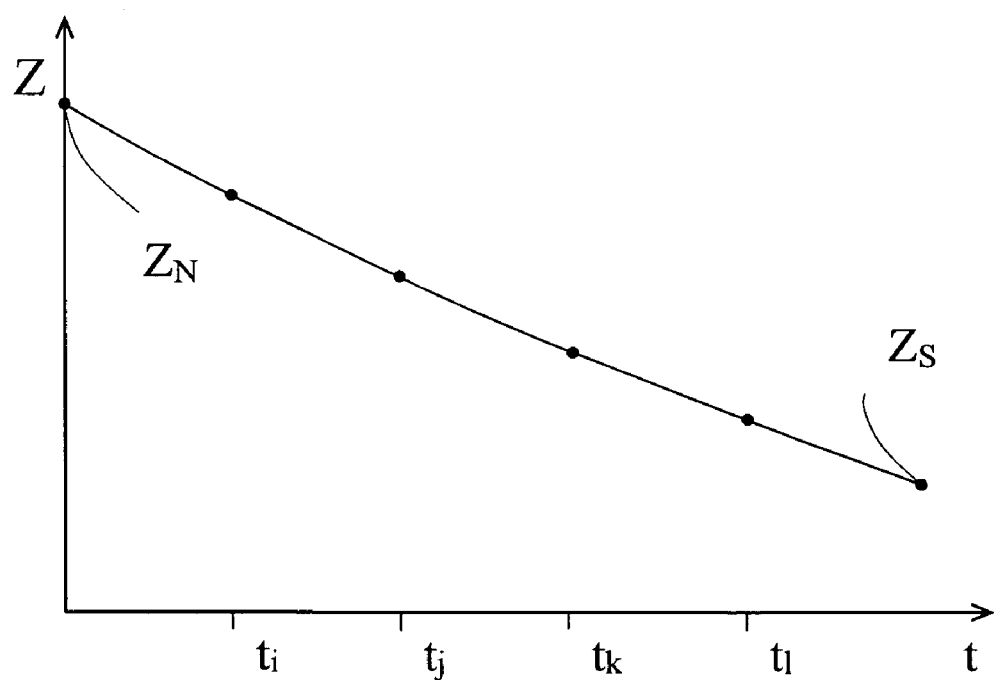
FIG. 2 is a graph showing decrease of impedance of the oil as the function of increase of the elapsed times according to the oil deterioration illustrated in FIG. 1.

The increase of the capacitance causes a decrease of the impedance Z of the oil according to the equation $Z=R+j(-1/\omega C)$. The decrease of the impedance in turn increases the current I which flows between the plates of the capacitive probe when an AC voltage V is applied across the plates. Such technology is well known in the art, and is specifically disclosed in U.S. Pat. No. 4,646,070. FIG. 2 illustrates during the normal oil deterioration a decrease of the impedance Z as a function of an increase of the used times of the oil. The impedance value "$Z_N$" is high for the new or unused oil, and the impedance value "$Z_S$" is low for the spent oil. Additionally, since oil is basically non-conductive, the capacitive reactance $j(-1/\omega C)$ or $X_c$, a component of the impedance is the predominant factor to govern the value of the impedance. Referring to FIG. 2, it will be appreciated that a user may periodically measure the impedance to determine the quality of the oil (denoted by dots). Measurement may range anywhere from continuous to infrequent.

Figure 3:
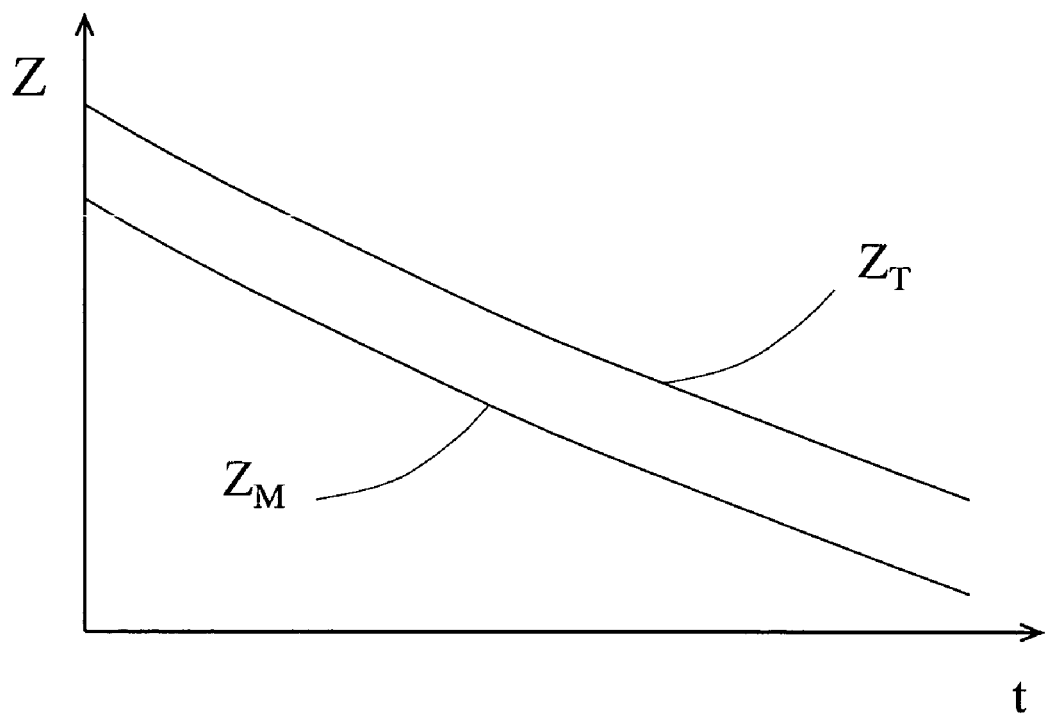
FIG. 3 is a graph showing relationship between a profile of measured impedance $Z_M$ and a profile of temperature compensated impedance $Z_T$.

However, it is noted that values of the dielectric constant of the oil are also influenced by the temperature variations, which cause variations of the capacitance of the capacitor so as to the impedance. Therefore, it is necessary to eliminate this temperature effect in the measurement by "compensating" variations of the measured impedance. This may be done by measuring a temperature of the oil and applying a correction factor to convert a value of the measured impedance $Z_M$ to a value of the actual or temperature compensated impedance $Z_T$. Also, a temperature compensated measurement can be made by always measuring the oil at a predetermined temperature. FIG. 3 shows relationship between a profile of the measured impedance $Z_M$ and a profile of the temperature compensated impedance $Z_T$ according to the used times, wherein the time is an independent variable that is expressed as a particular type of the oil usage.

Figure 4:
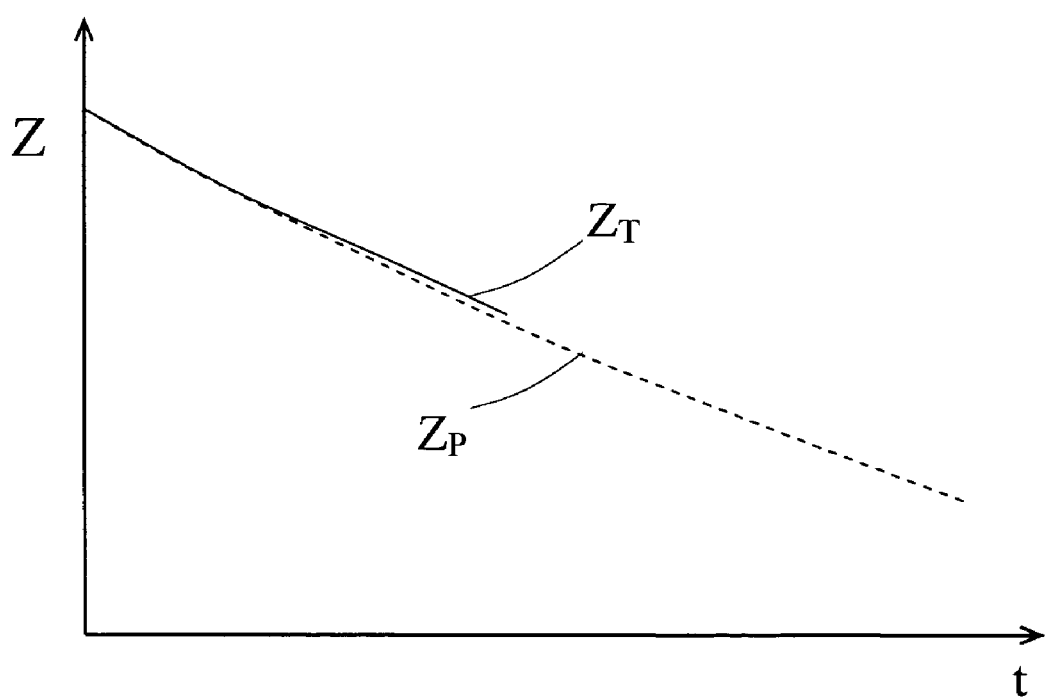
FIG. 4 is a graph showing a profile of predicted temperature compensated impedance $Z_P$, which is consistent with a profile of actual temperature compensated impedance $Z_T$.

FIG. 4 is a graph showing a profile of the predicted temperature compensated impedance $Z_P$ as compared with a profile of the actual or measured temperature compensated impedance $Z_T$. The profile of the predicted impedance $Z_P$ is anticipated, which decays smoothly as the function of the time. This indicates the normal deterioration of the oil. The predicted curve of the impedance $Z_P$ could be developed empirically through test measurements. From the illustrated example in FIG. 4, the actual impedance $Z_T$ closely follows the predicted impedance $Z_P$. This is a further indication of the normal oil deterioration. However, as it will be discussed later, certain influences can cause the predicted values to differ from the respective actual values of the impedance.

Referring to FIGS. 2-4, the oil deterioration has been shown in terms of the impedance measurement. Such impedance measurement may be conducted by placing a sensing capacitor in series with a known impedance to form a voltage divider, and applying an AC voltage across the capacitor and known impedance. The ratio of a voltage across the capacitor to a voltage across the known impedance is proportional to the impedance of the capacitor, which is the representation of the oil impedance.

It will be appreciated however, that the oil deterioration could also be represented and measured in terms of a current I flowing through the capacitor as a result of an applied constant voltage, or in terms of a voltage V developed across the capacitor as a result of an applied constant current. Any of these measurements may be performed using techniques well known in the electrical art. As in the case of the measured current and voltage they must also be temperature compensated.

Methods of measuring the various electrical properties of the capacitor are shown in FIGS. 5-7. The capacitor C can be constructed with two or more metal conductors in parallel having a spaced gap between two adjacent conductors for sufficient oil circulation. FIG. 5 is a circuit diagram which illustrates the impedance measurement using a voltage divider. An alternating voltage source $V_A$ applies a potential across a capacitor C connected to a reference impedance $Z_{ref}$ of known value. The impedance of the capacitor C represents the deterioration of the oil. In one embodiment, the reference impedance $Z_{ref}$ is a resistor.

FIG. 6 is a circuit diagram for the current measurement using a constant voltage source $V_0$. The current I through the capacitor C represents the deterioration of the oil.

FIG. 7 is a circuit diagram for the voltage measurement which uses a constant current source $I_0$. The voltage V across the capacitor C represents the deterioration of the oil.

FIG. 8 is a graph which illustrates profiles of the respective impedance, voltage, and current of the capacitor filled with an oil which deteriorates according to the elapsed times. It is of course noted that the impedance and voltage will decrease smoothly as the oil deterioration aggravates, and that the current will correspondingly increase as aggravation of the oil deterioration.

It will be appreciated that the impedance could be further separated into its imaginary component: capacitive reactance $X_c$, which is equal to $j(-1/\omega C)$, and real component: resistance R. Therefore, either of these measured components of the impedance, using procedures well known in the art, can provide an indication of the oil deterioration. Such measurements can be made using an alternating current analyzing device 30 including as an impedance analyzer of Agilent 4294A (Agilent, Palo Alto, Calif. USA) to obtain impedance, reactance, resistance, capacitance, and phase angle according to the respective single and multiple frequency tests. It is noted that phase angle can be determined by resistance and reactance.

Regarding the electronic configuration of the Agilent 4294A, it comprises a digital control, source, transducer, and vector ratio detector, wherein the source provides all analog signals of the AC excitation voltage having swept frequencies and variable voltage magnitudes that are applied to the sample, the transducer comprises a transform of the measured sample impedance into two AC signal voltages, the vector ratio detector comprises conversion of two AC voltages into digital data, and the digital control comprises digital data processing for outputting results of the sample measurement.

The device 30 can also be designed from electronic circuits based on the analog Lock-in principle, interfaced by including analog to digital convertors, which is further connected to the digital section for data acquisition (Princeton Applied Research, Oak Ridge, Tenn. USA). In addition, the digital analogy of the Lock-in principle, which is the digital correlation, can be additionally applied (Solartron, Farboroagh, Hampshire UK).

The above disclosed techniques apply AC signals with swept frequencies comprising a sinusoidal wave that sequentially varies frequencies to excite the oil in use as a measurement time elapses, wherein there is only one frequency at any point of time when the oil is excited. Instead of such one-frequency excitation mechanism, a poly-frequency excitation mechanism is also appropriate to construct the device 30 (Zahner-Elektrik Gmbh & CokG, Kronach Germany), which applies a plurality of sinusoidal waves having the respective different frequencies to excite the oil at any point of time. Such excitation could further employ the Fourier transform techniques.

Besides the above disclosed commercial instruments, the device 30 also can be constructed in application of an integrated circuit chip AD5933 (Analog Devices, MA USA). The chip is operated according to the mechanism of discrete Fourier transform (DFT), which generates real and imaginary data of an impedance at each of frequencies.

It will be appreciated that, if a measurement is conducted by applying a single frequency of an excitation signal, the periodic excitation signal from a device is capable of providing such single frequency comprising the respective square, triangular and sawtooth wave forms. Regarding the electrical circuits of the device for generating the single frequency of the periodic including an AC excitation signal such as voltage or current, the following are well known: RC phase-shift oscillator, Wien-bridge oscillator, Colpitts oscillator, Hartley oscillator, and square-wave generator (Aminian, Ali.; Kazimierczuk, Marian; Electronic Devices, a design approach, Pearson Prentice Hall 2004).

The above disclosure introduces well known technologies of applying a conventional capacitor serving as a sensor operated by the periodic including the AC electrical excitation for analyzing deterioration of the lubricating oil. However, as illustrated in the section of the prior art of this disclosure, there is still a room for improving the capacitor regarding its electrical characteristics, and output that is fundamental of the detection technology.

Figure 9:
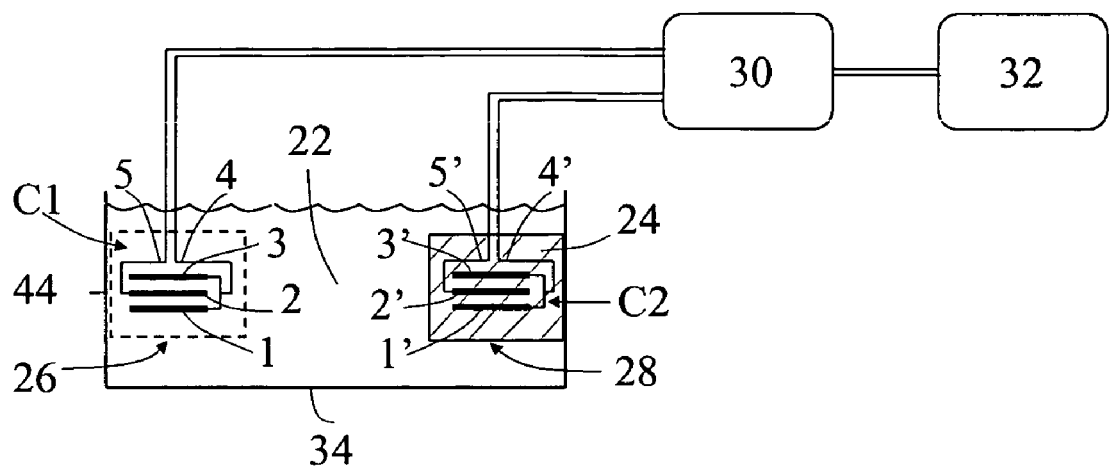
FIG. 9 is a diagram of an apparatus from a first preferred embodiment in the dual sensor configuration of the present invention which includes measurement and reference sensors having the respective identical sensing and referencing capacitive sensors, where a temperature compensated electrical property is developed.

Referring to FIG. 9, there is illustrated preferred embodiment of a measurement sensor 26 having a sensing capacitive sensor C1, which is an improved embodiment of the conventional capacitor having two plates. As illustrated, the sensing capacitive sensor C1 includes first, second and third identical metal plated conductors 1, 2 and 3, which are positioned equally spaced apart, in order, alignment and parallel with each other to thereby be bottom, middle and top electrodes. The first and third outer plated conductors 1 and 3 are the outer electrodes, and connected in parallel by a first lead wire serving as a first electrical pole 4, which forms a group of the integrated plated electrodes. The second plated conductor 2 is positioned at the middle of an air gap between the two outer plated conductors, and connected by a second lead wire serving as a second electrical pole 5. The sensing capacitive sensor C1 is connected to the AC analyzing device 30 through connection of the first and second electrical poles 4 and 5 to thereby receive an AC excitation of the device.

It will be appreciated that for an illustration purpose, the electrodes of the sensor C1 are positioned transversely. In fact, the electrodes can be positioned at any angles relative to the transverse orientation.

In addition, regarding an output of the electrical properties of the sensing capacitive sensor C1, it is equivalent to that of two conventional capacitors connected in parallel if the paired plated electrodes 1 and 2 are the same as the paired plates of the conventional capacitor. Therefore, the sensing capacitive sensor C1 has the same output as that of the two conventional capacitors. However, the sensing capacitive sensor C1 only has three plated conductors, as compared with four plates of the two connected capacitors. Thus, the sensing capacitive sensor C1 has smaller sizes as compared with those of the two connected capacitors. Therefore, the present invention sensing capacitive sensor C1 possesses properties of having the same output of the raw electrical information of an oil sample but smaller physical sizes, including less one electrode, as compared with two paraellelly connected capacitors. These properties make the present invention sensing capacitive sensor be advantageous in the sensor miniaturization, which is one of the key aspects of the sensor technologies.

Further Referring to FIG. 9, there is illustrated that the first and second electrical poles 4 and 5 of the sensing capacitive sensor C1 are connected to the alternating current analyzing device 30 that applies an AC voltage to the sensor. It will be appreciated that when a positive voltage is applied to the first electrical pole 4 and a negative voltage is applied to the second electrical pole 5, the outer electrodes 1 and 3 are positively charged and middle electrode 2 is negatively charged. Therefore, the two positively charged outer electrodes shield the negatively charged middle inner electrode, and the outermost electrical field of the sensor C1 is symmetrical relative to the middle electrode.

The same situation also exists for the outer electrodes to shield the middle electrode when a positive voltage is applied to the middle plated electrode 2 and a negative voltage is applied to the outer plated electrodes 1 and 3. Therefore, the sensing capacitive sensor C1 has unique electrical properties, including the middle electrode that is always shielded by two outer electrodes and outermost electrical field that is symmetrical to the surrounding electromagnetic environment. These properties are critical to the present invention sensor and method that applies the AC electricity.

It can be realized that the disclosed embodiment of the sensing capacitive sensor C1 has the least number of the plated electrodes as compared with allowable number of the plated integrated electrodes according to the spirit and scope of the present invention. Broadly speaking, a general embodiment of the capacitive sensor C1 could have a total of an odd number of the identical plated electrodes, which are positioned equally spaced apart, in order, alignment and parallel with each other. Within the electrodes, the odd numbered plated electrodes are connected in parallel by a first lead wire serving as a first electrical pole to thereby form a first group of the integrated electrodes. Two outermost and middle plated electrodes in the first group serve as the respective outermost electrodes and innermost electrode of the sensor. The even numbered plated electrodes are connected in parallel by a second lead wire serving as a second electrical pole to form a second group of the integrated electrodes.

Now referring to FIGS. 9-11, 13 and 14, there is illustrated method in accordance with a first preferred embodiment of the present invention applying the improved capacitive sensors for detecting oil conditions including a top level of the predetermined threshold amount of the oil, or an abnormal deterioration of the oil which occurs in the presence of water, or a normal deterioration of the oil which occurs in the absence of water and contains a remaining usage of the oil.

Figure 10:
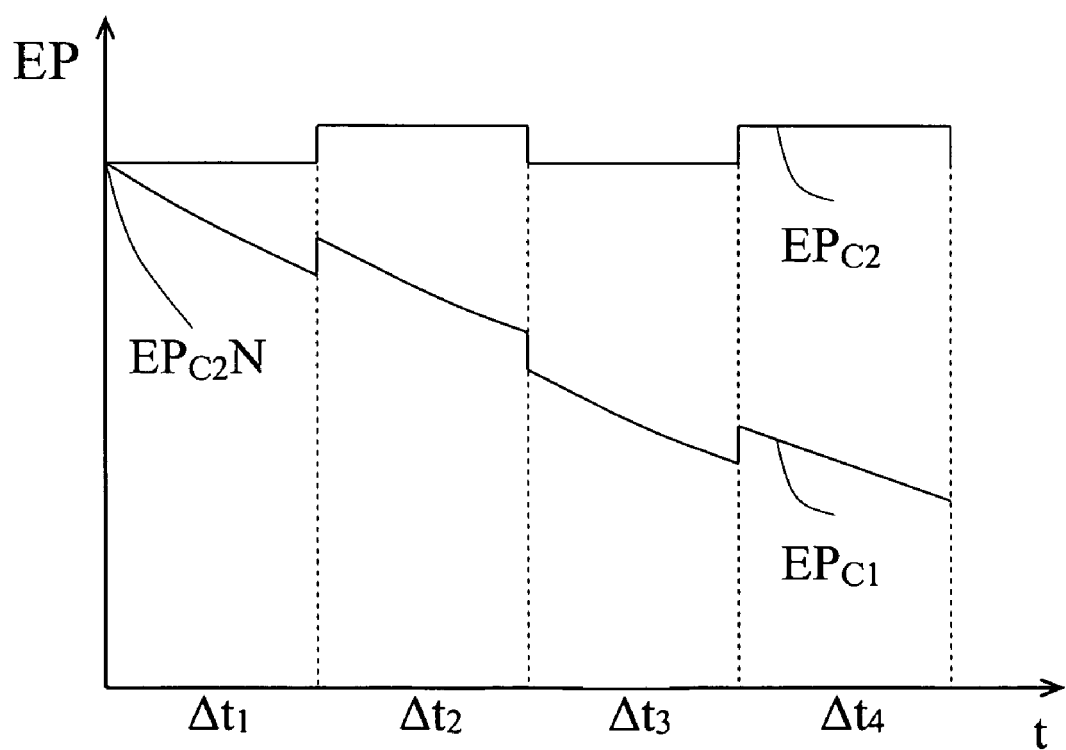
FIG. 10 is a graph which shows electrical property profiles of the respective sensing and referencing capacitive sensors without the temperature compensation.

In this embodiment, a reference sensor 28 having a referencing capacitive sensor C2 is utilized to compensate variations of the measured electrical properties of the sensing capacitive sensor C1, which are induced by the temperature variations. The referencing capacitive sensor C2, which is identical to the sensing capacitive sensor, includes first, second and third plated electrodes 1', 2' and 3', and first and second electrical poles 4' and 5' that are also connected to the AC analyzing device 30. The method includes:

(a) providing an oil 22 in use which is known not to contain water and disposed in an oil system including an oil reservoir of a machine such as a crankcase 34 of an engine or a container of an electrical transformer;

(b) providing a reference oil 24 disposed in a sealed container which is located in a common temperature environment with the oil 22. The reference oil 24 is free of water;

In a preferred embodiment, the reference oil 24 has the same thermal properties as the oil 22. That is, temperature variations cause the electrical properties of the reference oil 24 and the electrical properties of the oil 22 to change in a like manner. Also in the preferred embodiment, the reference oil can be either (1) an unused oil, or (2) a spent oil, or (3) a partially spent oil. For example, the reference oil 24 which is illustrated in FIG. 10 is the unused oil of the same brand and type as the oil 22.

(c) providing a measurement sensor 26 including a sensing capacitive sensor C1;

In the preferred embodiment, the measurement sensor 26 may further include a container that has a plurality of openings for allowing oil circulation in addition to protect the sensing capacitive sensor placed inside of the container. Therefore the container is represented to be the dashed lines in FIG. 9.

(d) providing a reference sensor 28 which includes a referencing capacitive sensor C2 that is identical to the sensing capacitive sensor C1. The reference sensor 28 includes the sealed container wherein the referencing capacitive sensor C2 is fully immersed in the reference oil 24.

Referring to FIG. 9, the sealed container is represented as a closed square. It will be appreciated that mechanical parameters are identical to the containers of the respective measurement and reference sensors 26 and 28. The containers are preferably made of metals or metal alloys so that they provide similar electromechanical and electromagnetical properties to the respective sensors. In addition, it will be appreciated that the measurement sensor 26 and reference sensor 28 can be arranged into an integrated mechanical unit.

(e) positioning the measurement sensor 26 to the oil system wherein the sensing capacitive sensor C1 is fully immersed in the oil 22;

(f) using a measuring device for measuring an electrical property $EP_{C1}$ of the sensing capacitive sensor C1 and electrical property $EP_{C2}$ of the referencing capacitive sensor C2 from a first measurement, wherein the electrical property is one of:

the impedance of the sensing capacitive sensor and impedance of the referencing capacitive sensor;

the current passing through the sensing capacitive sensor and current passing through the referencing capacitive sensor;

the voltage developed across the sensing capacitive sensor and voltage developed across the referencing capacitive sensor;

(g) combining the electrical property $EP_{C1}$ of the sensing capacitive sensor with the electrical property $EP_{C2}$ of the referencing capacitive sensor to obtain a first measured temperature compensated electrical property of the sensing capacitive sensor, which represents a first measured temperature compensated electrical property $EP_{T,i}(M)$ of the oil. The oil property may represent deterioration of the oil 22. Here the symbol "$EP_{T,i}(M)$" is used to represent the property of the oil, where the subscribed letter "T" indicates the temperature compensation, and the subscribed letter "i" indicates the first measurement. In addition, the letter "M" means the electrical property "EP" which is obtained through measurement.

Referring to FIG. 9, the electrical property $EP_{C1}$ of the sensing capacitive sensor and the electrical property $EP_{C2}$ of the referencing capacitive sensor are combined in the measurement device 30 to result in the first measured temperature compensated electrical property of the sensing capacitive sensor, which can be routed to a display 32 for presentation to the user under the user's choice.

Figure 11:
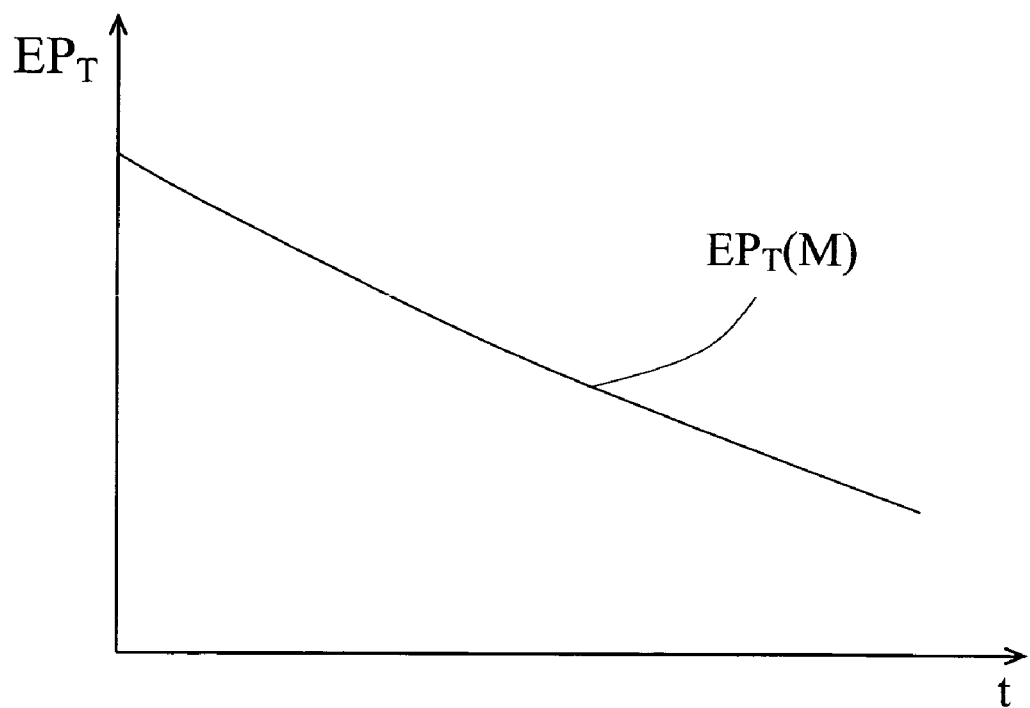
FIG. 11 is a graph which shows a profile of measured temperature compensated electrical properties $EP_T(M)$ of the sensing capacitor as derived from FIG. 10.

Referring now to FIGS. 10 and 11, there is illustrated how variations of the electrical property $EP_{C1}$ can be compensated by applying the referencing capacitive sensor C2 from the present invention. In this embodiment, the reference oil is the unused oil or the new oil of the same brand and type as the oil 22. As illustrated, during the time interval $\Delta t_1$, the electrical property $EP_{C2}$ of the referencing capacitive sensor has a constant value $EP_{C2}N$. However, during the time period $\Delta t_2$ the value of the electrical property $EP_{C2}$ increases due to a change of the oil temperature. Similarly, during the time interval $\Delta t_3$ the value returns to the normal one, and during the time period $\Delta t_4$ the value again increases due to a temperature change. In addition, it will be appreciated that the reference oil is sealed separately, so that it is not subject to conditions caused by operation of the machine, and thus it does not deteriorate during the entire life of its usage. This is illustrated by its vale $EP_{C2}N$ that is unchanged over the times, wherein $EP_{C2}N$ is a normal value of the electrical property of the referencing capacitor filled with the new oil.

Such behavior of the electrical property $EP_{C2}$ is utilized as a baseline to correct or compensate the electrical property $EP_{C1}$ of the sensing capacitive sensor filled with the oil, which is also influenced by the temperature variations. In addition, the electrical property of the sensing capacitive sensor is also influenced by the aggravation of the oil deterioration according to the oil usage of the elapsed times. Therefore, the oil is changed starting from a new oil when the oil is unused to a spent oil when the oil is completely used. For this reason, the initial property of the sensing capacitive sensor has the same value as the $EP_{C2}N$ of the referencing capacitive sensor.

It will be appreciated that the temperature change effects the electrical property $EP_{C1}$ and electrical property $EP_{C2}$ in an identical fashion since both two sensors are in the same temperature environment, the oil 22 in use and reference oil 24 have the same or similar thermal properties, and two sensors are identical. Therefore, by combining electrical property $EP_{C1}$ and electrical property $EP_{C2}$ according to a below-cited equation [1], the result is a measured temperature compensated electrical property $EP_T(M)$ of the sensing capacitive sensor, which may be the representation of the oil deterioration.

It will be appreciated that the shown curve for the electrical property in FIG. 11 is one for the impedance or voltage. If for the current, the curve would be as that shown in FIG. 8.

Referring to FIG. 11, there is illustrated that the measured electrical properties of the respective sensors C1 and C2 have been combined. The result is a measured temperature compensated electrical property $EP_T(M)$ at each measurement over the entire life of usages of the oil starting from the new oil which deteriorates to be the spent oil. Therefore, it forms a profile of the measured temperature compensated electrical properties $EP_T(M)$ of the oil.

In a preferred embodiment of combining the electrical properties of the respective two capacitive sensors, variations of the electrical property $EP_{C1}$ of the sensing capacitive sensor C1 due to the temperature variations are essentially subtracted from the same variations of the electrical property $EP_{C2}$ of the referencing capacitive sensor C2 in accordance with the following equation [1]:

$$EP_T(M)=EP_{C1}-EP_{C2}+EP_{C2}N \qquad [1]$$

From the equation, the value $EP_{C2}N$ can be a value including the nominally measured value of $EP_{C2}$, which positions $EP_T(M)$ along the positive values of the y axis in FIG. 11. Referring to the figure, the y axis represents the temperature compensated electrical properties $EP_T$ of an oil including the new, partially spent and spent oil. The x axis is each of the elapsed times during deterioration of the oil.

However, it will be another appreciated that other methods of combining $EP_{C1}$ and $EP_{C2}$ such as $(EP_{C1}-EP_{C2})$ could also be employed so long as the electrical property $EP_{C2}$ of the referencing capacitive sensor C2 is utilized to remove the temperature effects from the electrical property $EP_{C1}$ of the sensing capacitive sensor C1. Further, if combining the properties through $(EP_{C2}-EP_{C1})$, a deterioration profile of the oil can be obtained, which is similar to the one in FIG. 1.

Also, referring to FIGS. 9-11, and as previously mentioned including in step (f), the electrical property could be one of the components of the impedance, resistance R or capacitive reactance $X_c$, rather than the total composite impedance. Measurement procedures and equipments well known in the art could be used to make such measurements, for this or other oil measurement methods disclosed herein.

It will be appreciated that as described herein the "unused" oil is a new or fresh oil which is essentially free of contaminants. The "partially spent" oil is an oil that has been in use for some period of time, and therefore has some build up of contaminants. Also, the profile of the measured temperature compensated electrical properties $EP_T(M)$ shown in FIG. 11 utilizes the time as the independent variable. However, other parameters besides the time could also be utilized. For example in a motor vehicle a profile of the temperature compensated electrical properties $EP_T$ could be expressed as the function of a usage of the oil, such as traveled miles rather than the used times.

Figure 12:
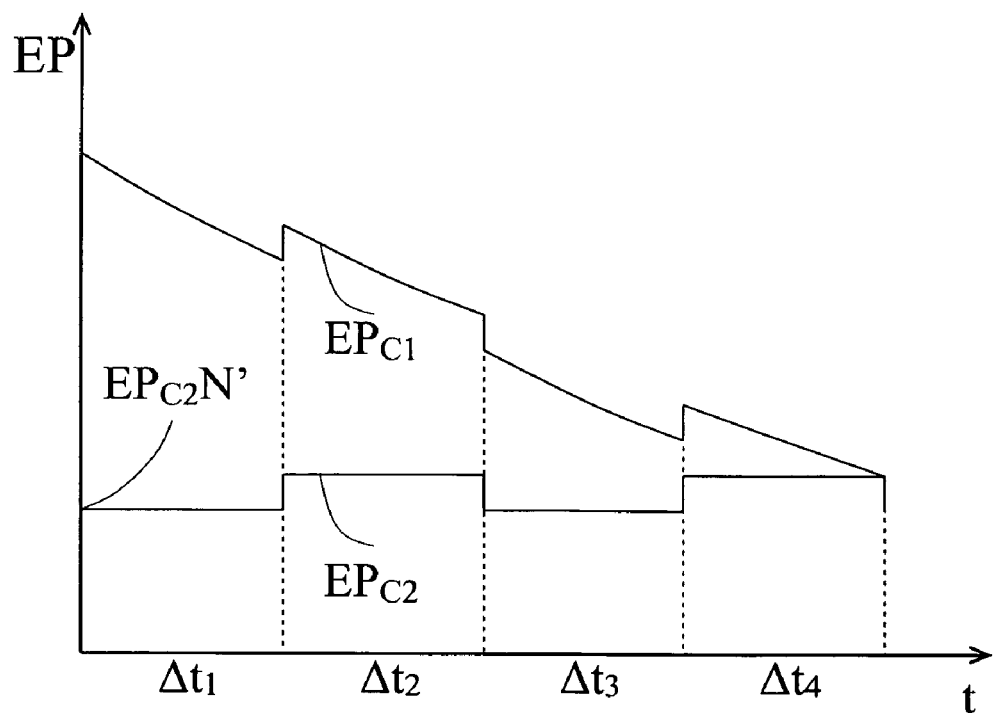
FIG. 12 is a second graph to illustrate electrical property profiles of the respective sensing and referencing capacitive sensors without temperature compensation.

FIG. 12 illustrates an alternative method for compensation of the temperature effects. In this embodiment the spent oil rather than the unused oil is used as the reference oil. Therefore, the sensing capacitive sensor C1 is immersed in the oil 22 as before, but the referencing capacitive sensor C2 is immersed in the reference oil 24 which is the spent oil having its normal value $EP_{C2}N'$. The spent oil is an oil with large concentrations of contaminants, and therefore whose lubricating properties are effectively exhausted. The spent oil used as the reference oil 24 preferably has the same thermal properties as the oil 22. In the respective time periods $\Delta t_2$ and $\Delta t_4$ a same change in oil temperature causes the same increase in both electrical properties $EP_{C1}$ and $EP_{C2}$.

It will be appreciated that if the measured electrical properties of the respective sensors C1 and C2 in FIG. 12 have been combined as before, a resulted profile of the measured temperature compensated electrical properties $EP_T(M)$ is identical to the profile shown in FIG. 11. It will be further appreciated that through the later discussions, the above disclosed measured properties $EP_T(M)$ can serve as the representation of the oil deterioration or oil level according to the respective situations.

In addition, following the above disclosed steps (a) to (g), it can obtain a profile of the predicted temperature compensated electrical properties $EP_T(P)$ for the oil 22, wherein the letter "P" means the electrical properties "EP" which are predicted according to the respective known usages. The profile represents aggravation of the normal deterioration of the oil in its entire life of usages if the oil is dry. The profile includes a temperature compensated electrical property $EP_{T,N}$ for the oil when it is new or unused, and a temperature compensated electrical property $EP_{T,S}$ for the oil when it is spent. Between the temperature compensated electrical properties $EP_{T,N}$ and $EP_{T,S}$, there are various different temperature compensated electrical properties $EP_{T,PS}$ for the respective partially spent oils. The temperature compensated electrical properties $EP_{T,PS}$ represent the oil when it is dry at different stages of the oil deterioration according to the respective oil usages.

It will be appreciated that for illustration of the present invention, the definition of "a profile of measured temperature compensated electrical properties $EP_T(M)$" is identical to the respective definitions "a measured temperature compensated electrical property profile", "a measured property profile", and "a profile of the measured properties $EP_T(M)$". Similarly, the definition of "a profile of predicted temperature compensated electrical properties $EP_T(P)$" is identical to the respective definitions "a predicted temperature compensated electrical property profile", "a predicted property profile", and "a profile of the predicted properties $EP_T(P)$". In addition, the "measured temperature compensated electrical property (properties) $EP_T(M)$" and "predicted temperature compensated electrical property (properties) $EP_T(P)$" can be simply addressed as the respective "measured property (properties) $EP_T(M)$" and "predicted property (properties) $EP_T(P)$". Similarly, the "temperature compensated electrical property $EP_{T,N}$", "temperature compensated electrical property $EP_{T,S}$" and "temperature compensated electrical property $EP_T$" can be simply addressed as the respective "property $EP_{T,N}$", "property $EP_{T,S}$" and "property $EP_T$".

The profile of the predicted properties $EP_T(P)$ for the oil can be obtained from various previously disclosed methods. Hereafter is an example for experimentally simulating the entire deterioration for the oil 22 when it is dry to obtain the profile of the predicted properties $EP_T(P)$.

When the oil is new or unused which obviously does not contain water, the new oil is tested following the above disclosed steps (a) to (g), which results in the property $EP_{T,N}$. Then the dry new oil is experimentally used for a purpose to make it deteriorated according to a predetermined period of the experimental times. It will be appreciated that experimental conditions are the same as or mostly close to conditions of the actual usage of the oil. The dry new oil then becomes a partially spent dry oil to have a predetermined degree of deterioration which correlates to the experimental times. Then the dry oil having the known degree of deterioration is measured following the above disclosed steps (a) to (g), which results in a property $EP_{T,PS}$ that is a predicted property $EP_T(P)$ according to the known degree of the oil deterioration.

The dry oil having the known degree of deterioration is experimentally used for the second time according to the same predetermined period of the experiment times, where all the experimental conditions are kept the same for the entire experiment of oil deterioration. Thus it causes the dry oil further partially deteriorated. Then the further partially deteriorated oil is measured again following the above disclosed steps (a) to (g), which results in a temperature compensated electrical property that represents a larger degree of the oil deterioration, as compared with the prior property $EP_{T,PS}$.

Following this manner to complete the oil deterioration, the oil is deteriorated to the spent oil. Therefore, the profile of the predicted temperature compensated electrical properties $EP_T(P)$ can be established, which represents the normal deterioration that occurs for the oil 22 if it is dry. It will be appreciated that the reference oil also can be applied for obtaining such profile of the predicted electrical properties $EP_TP$ since the reference oil is a dry oil having the same brand and type as the oil 22, which is disclosed before.

Therefore, the first embodiment of the present invention method continually comprises the following step:

(h) following the steps (a) to (g) establishing a predicted temperature compensated electrical property profile for the oil, which represents the normal oil deterioration, the predicted property profile includes a property $EP_{T,N}$, which is equal to a measured property $EP_T(M)$ of the oil if it is unused or new and dry, and another electrical property $EP_{T,S}$, which is equal to a measured property $EP_T(M)$ of the oil if it is spent and dry.

Figure 13:
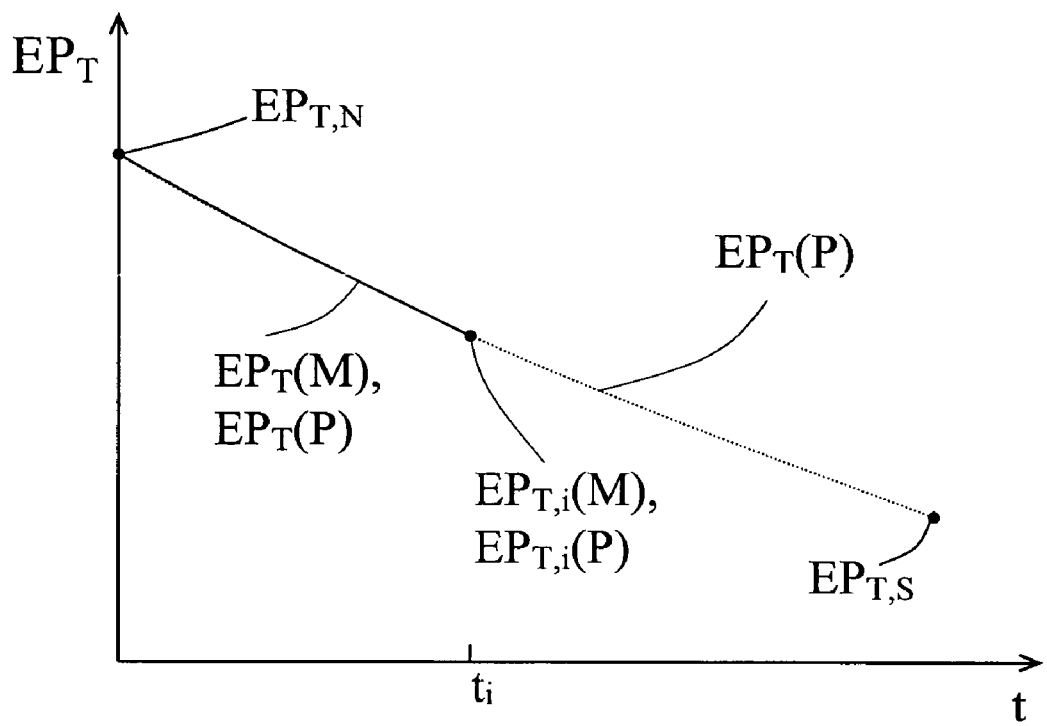
FIG. 13 is a graph showing profiles of the respective measured and predicted temperature compensated electrical properties during a normal deterioration of the oil, where the profiles are presented in accordance with the independent variable of the elapsed times.
Figure 14:
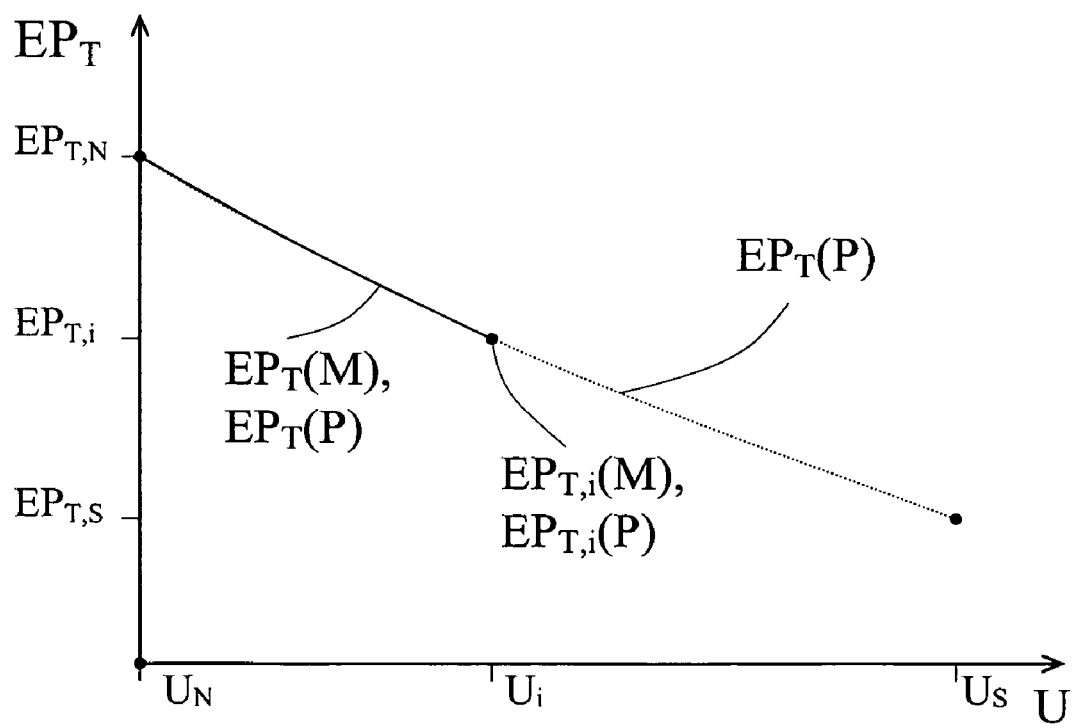
FIG. 14 is a graph showing the same profiles of the respective measured and predicted temperature compensated electrical properties during the normal deterioration of the oil in FIG. 13. However, the profiles are presented according to the independent variable of usage of the oil which includes the used times or the traveled miles.

Now the normal oil deterioration, which has been briefly disclosed in FIG. 4, will be illustrated in detail in FIGS. 13 and 14. FIGS. 13 and 14 illustrate the same situation of the normal oil deterioration, where a partial profile of the measured properties $EP_T(M)$ is illustrated, which is consistent with a corresponding section of the profile of the predicted properties $EP_T(P)$. It will be appreciated that, for a comparison with an abnormal oil deterioration in later discussion, only the partial of the measured property profile for the normal oil deterioration is presented in the respective figures.

Referring to FIG. 13, the predicted property profile includes the properties of the respective new oil, spent oil and partially spent oils, which is presented as the dashed line. The partial of the measured property profile, which is presented as the solid line, includes the properties of the respective new oil and oil in use. The partial profile of the measured properties $EP_T(M)$ illustrates that the new oil has been used thus deteriorated in a period of times that ends at a point of time $t_i$, which corresponds to a measured property $EP_{T,i}(M)$. The measured property $EP_{T,i}(M)$ is a first measured property $EP_T(M)$ from a first measurement which serves an example to illustrate how the present invention applies measured and predicted properties to determine conditions of the oil. Accordingly, the predicted property profile of the oil also contains a predicted property $EP_{T,i}(P)$ according to the point of time $t_i$ which serves as a first predicted property $EP_T(P)$ of the example of the present invention. As illustrated, the first measured property $EP_{T,i}(M)$ has the same value, as compared with that of the first predicted property $EP_{T,i}(P)$.

Now referring to FIG. 14, it illustrates the same profiles of the respective measured and predicted properties as disclosed in FIG. 13. However, instead of using the time as the independent variable, FIG. 14 applies an actual usage U of the oil as the variable, which can also be simply addressed as "usage" in the following disclosure. Therefore, the properties $EP_{T,N}$ and $EP_{T,S}$ of the respective new and spent oil are related to the respective usages $U_N$ and $U_S$. The usage $U_S$ represents a number of the traveled miles or used times of the spent oil during the entire life of usages of the oil which is changed from the new oil to the spent oil. It will be appreciated that due to the consistency between the predicted and measured properties, the electrical properties of the respective new and spent oil are presented as the respective same properties $EP_{T,N}$ and $EP_{T,S}$ regarding their respective measured and predicted properties $EP_T(M)$ and $EP_T(P)$. Accordingly, a full range of usages of the oil $\Delta U_F=(U_S-U_N)$ is defined relative to the electrical property change $(EP_{T,N}-EP_{T,S})$. In addition, FIG. 14 further illustrates that the first measured property $EP_{T,i}(M)$ is consistent with the first predicted property $EP_{T,i}(P)$ related to the same first usage $U_i$, which represents the normal deterioration of the oil.

Obtaining the above mentioned information, the first embodiment of the present invention continually comprises the following steps:

(i) establishing a full range of actual usages for the oil as $\Delta U_F=(U_S-U_N)$ according to change of the properties as $(EP_{T,N}-EP_{T,S})$, wherein a symbol U represents an actual usage of the oil which is an independent variable to the property $EP_T$, so that the $U_N$ is an actual usage of the oil which is new or unused and the $U_S$ is an actual usage of the oil which is spent;

(j) defining a first measured normalized remaining usage ratio $R_{M,i}$ of the oil having the first measured property $EP_{T,i}(M)$ as:

$$R_{M,i}=[EP_{T,i}(M)-EP_{T,S}]/[EP_{T,N}-EP_{T,S}],$$

wherein the $R_{M,i}$ ranges from one for the oil that is new or unused and dry to zero for the oil that is spent and dry, which can be simply addressed as "a first measured ratio $R_{M,i}$".

And further defining a first measured remaining usage of the oil as $R_{M,i}\Delta U_F=R_{M,i}\times(U_S-U_N)$ from the first measurement.

Accordingly, a first measured normalized deterioration ratio $D_{M,i}$ of the oil having the first measured property $EP_{T,i}(M)$ can be defined as:

$D_{M,i}=[EP_{T,N}-EP_{T,i}(M)]/[EP_{T,N}-EP_{T,S}]$, ranging from zero for the new oil to one for the spent oil, which can be simply addressed as "a first measured ratio $D_{M,i}$".

In addition, it can be similarly established for a predicated normalized remaining usage ratio $R_P$, which can be simply addressed as "a predicted ratio $R_P$" according to a predicted property $EP_T(P)$ from the predicted property profile. For example, there is the first predicted property $EP_{T,i}(P)$ in the respective FIGS. 13 and 14 according to the respective first time $t_i$ and usage $U_i$. A first predicated ratio $R_{P,i}$ is equal to $[EP_{T,i}(P)-EP_{T,S}]/[EP_{T,N}-EP_{T,S}]$, which leads to a first predicted remaining usage ($R_{P,i}\Delta U_F$), and a first predicated normalized deterioration ratio: $D_{P,i}=[EP_{T,N}-EP_{T,i}(P)]/[EP_{T,N}-EP_{T,S}]$ that can be simply addressed as "a first predicted ratio $D_{P,i}$".

According to the illustration of FIG. 14, it will be appreciated that the first measured ratio $R_{M,i}$ is consistent with the first predicted ratio $R_{P,i}$ according to the same first usage $U_i$. Therefore the first measured remaining usage ($R_{M,i}\Delta U_F$) is also consistent with the first predicted remaining usage ($R_{P,i}\Delta U_F$). In this situation, it concludes the normal deterioration of the oil, plus the first measured remaining usage which is confirmed as the remaining actual usage.

Therefore, continuing from the previous step (j) of the method, the present invention has the following step:

(k) from the predicted property profile, determining a first predicted property $EP_{T,i}(P)$ according to the same first actual usage $U_i$ as compared with the first measured property $EP_{T,i}(M)$ related to the first measurement, from which establishing a first predicated normalized remaining usage ratio as $R_{P,i}=[EP_{T,i}(P)-EP_{T,S}]/[EP_{T,N}-EP_{T,S}]$ and a first predicted remaining usage ($R_{P,i}\Delta U_F$) of the oil;

It also can conclude that determining a normal deterioration of the oil which occurs in the absence of water if the first measured remaining usage ($R_{M,i}\Delta U_F$) is similar to the first predicated remaining usage ($R_{P,i}\Delta U_F$), and confirming the first measured remaining usage which represents a remaining actual usage of the oil.

It will be appreciated that the similarity between the measured and predicted remaining usages can always be easily and quantitatively defined by a predefined threshold value in application of the present invention.

It will be further appreciated that the above mentioned first measured or first predicted ratio $R_{M,i}$ or $R_{P,i}$ which has been derived according to an approximation of the linear relationship between the change of the properties as ($EP_{T,N}-EP_{T,S}$) and the range of usages as ($U_S-U_N$). Therefore, the first measured remaining usage ($R_{M,i}\Delta U_F$) is a close approximated value to a remaining actual usage.

It will be additionally appreciated that a normalized first measured remaining usage ratio R' also could be mathematically derived, which is based on a possible nonlinear relationship between the change of the properties as ($EP_{T,N}-EP_{T,S}$) and range of usages as ($U_s-U_N$).

However, despite shapes of the respective predicted and measured property profiles, a first measured remaining actual usage is always correctly presented as: $\Delta U_M=(U_S-U_M)$, where $U_M$ is a first measured actual usage of the oil which is corresponding to the first measured property $EP_{T,i}(M)$. Referring to FIG. 14, $U_i$ is the first usage of the oil at the traveled miles i or spent times i, which correlates to the both first measured and predicted properties $EP_{T,i}(M)$ and $EP_{P,i}(P)$ during the normal oil deterioration. Therefore, a first predicted remaining actual usage is $\Delta U_P=(U_S-U_P)$ wherein $U_P$ is a first predicted actual usage of the oil which is corresponding to the first predicted property $EP_{T,i}(P)$. $\Delta U_P$ is equal to the first measured remaining actual usage $\Delta U_M=(U_S-U_M)=(U_S-U_i)$ since the respective predicted and measured actual usages $U_P$ and $U_M$ are equal to the usage $U_i$. This also proves the normal deterioration of the oil, and confirms the measured remaining actual usage.

Now referring to FIG. 14 again, there is illustrated that up until the first usage $U_i$, the predicted properties $EP_T(P)$ are consistent with the measured properties $EP_T(M)$. This indicates the oil in use which is deteriorating in a predicted manner. However, as will be subsequently discussed, events occurring at the first usage $U_i$ cause a value of a measured property $EP_T(M)$ to differ from a value of a predicted property $EP_T(P)$.

Figure 15:
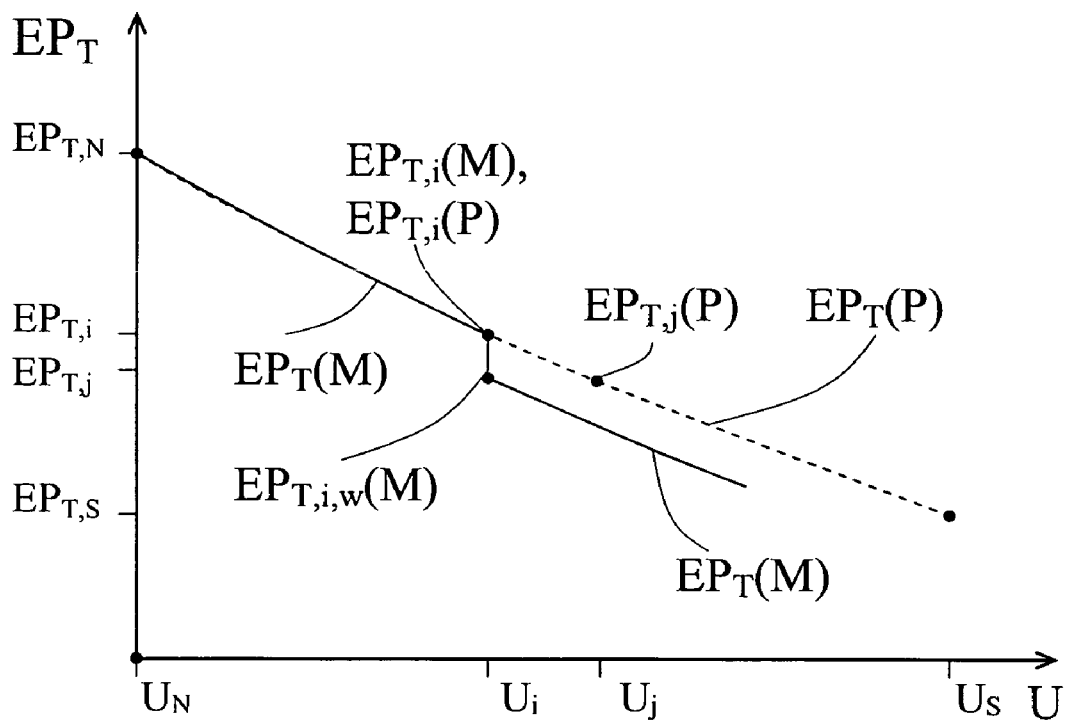
FIG. 15 is a graph showing the same curves in FIG. 14 including the predicted temperature compensated electrical property profile and a measured temperature compensated electrical property profile according to usages of the oil. The difference is that the measured property profile staring at an usage $U_i$ has a sudden change, which illustrates extra deterioration of the oil than it should be.

Reference to FIG. 15 illustrates detection of the abnormal deterioration of the oil which occurs in the presence of water, wherein it is at the first usage $U_i$ that the presence of water happens. As illustrated in FIG. 15, there is a sudden change of the first measured property $EP_{T,i}(M)$ from the first measurement to a second measured property $EP_{T,i,w}(M)$ from a second measurement, as compared with the first predicted property $EP_{T,i}(P)$ which represents the normal oil deterioration that occurs in the absence of water. In addition, since the first usage the measured property profile consistently departs from the predicted property profile.

Figure 16:
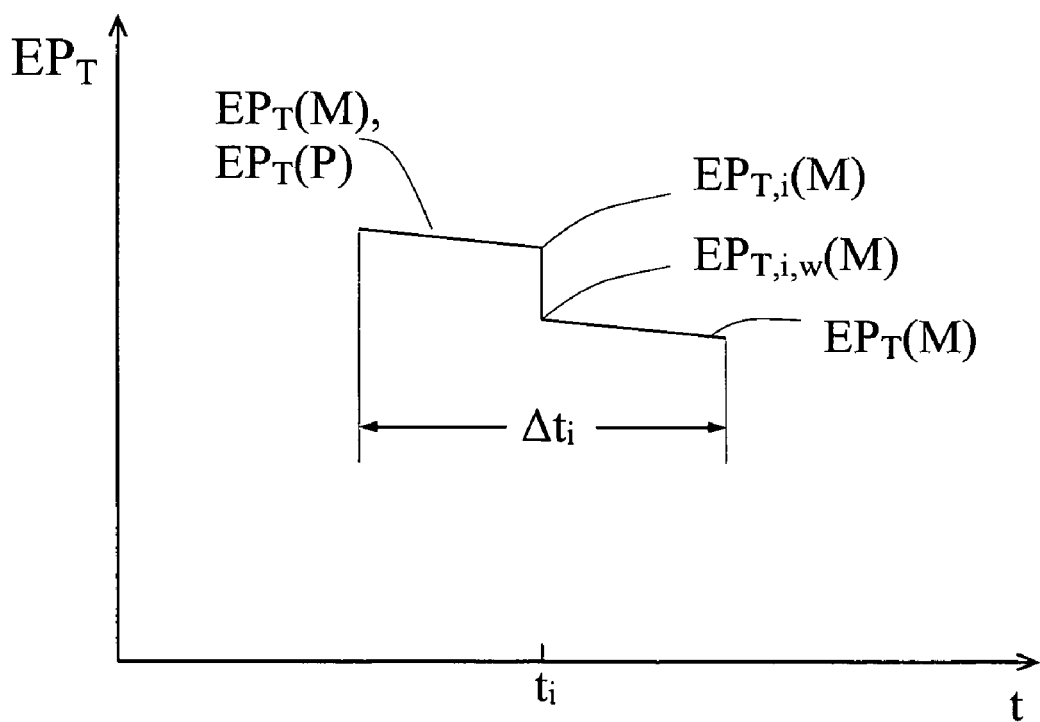
FIG. 16 is a graph which magnifies a section of the measured property profile in FIG. 15 wherein the profile has the sudden change of the property at the usage $U_i$.

For a detailed illustration, FIG. 16 magnifies a section of the measured property profile according to the first usage $U_i$ when the sudden change of the measured properties occurs. However, the time is used as the independent variable in FIG. 16. In this embodiment, the likely presence of water in the oil is detected. For example, in an internal combustion engine, a head gasket could be partially ruptured at a small scale. An initial presence of the small rupture allows water suddenly to enter into the oil system, which causes the corresponding sudden change of the measured property $EP_T(M)$. It will be appreciated that the electrical property of the sensing capacitive sensor C1 could possibly be affected by other factors, however the sudden change in electrical properties is likely to be the result of the water contamination. This is because the dielectric constant of water is significantly larger (approximately 3-4 times) than the dielectric constant of an oil.

The presence of water in the oil will reduce the impedance of the sensing capacitive sensor or the voltage developed across the sensor, and correspondingly increase the current flowing through the sensor filled with the mixture of water and oil. Therefore, the fact of suddenly presenting water in the oil will cause the sudden change of the electrical properties of the sensing capacitive sensor, which is presented as extra deterioration of the oil, as compared with the normal deterioration that is determined by the predicted property $EP_T(P)$.

Referring to FIG. 16 again, there is illustrated that it is at the first moment $t_i$ of the time interval $\Delta t_i$, the first measured property $EP_{T,i}(M)$ of the impedance or voltage from the first measurement has a sudden drop to the second measured property $EP_{T,i,w}(M)$ from the second measurement, wherein the letter w denotes the presence of water. As further illustrated, during the rest of the time interval $\Delta t_i$, the measured property profile continuously decreases to align with its initial slope, or an initial pattern of changing the properties, which exists prior to the first moment $t_i$. This is because of the continuous presence of a constant small amount of water due to a dynamic balance of water in the oil such as when an extra amount of water could be evaporated.

As compared with FIG. 16 which describes the water presence during the small time interval $\Delta t_i$, FIG. 15 particularly illustrates how the presence of water in the oil causes a change of the measured temperature compensated electrical property and the corresponding remaining usage as well, as compared with the respective predicted values.

Referring to FIG. 15 since the first usage $U_i$, the oil mixed with the constant small amount of water exhibits a pattern of the measured properties $EP_T(M)$, which is the same as a pattern of the predicted properties $EP_T(P)$ for the oil without the constant small amount of water. Therefore, a value of the second measured property $EP_{T,i,w}(M)$ for the oil mixed with the constant small amount of water is equal to a value of a predicted property $EP_{T,j}(P)$ for the oil without the constant small amount of water according to the profile of the predicted properties $EP_T(P)$. Apparently, the value of the predicted property $EP_{T,j}(P)$ is less than that of the first predicted property $EP_{T,i}(P)$. This means that the oil which is mixed with the constant small amount of water acts as a dry oil which is spent more than it should be, or which has extra deterioration as compared with deterioration predicted by the first predicted property $EP_{T,i}(P)$. Therefore, a second measured normalized remaining usage ratio for the oil mixed with the constant small amount of water at the first usage $U_i$ is equivalent to a predicted normalized remaining usage ratio $R_{P,j}$ for the oil at an usage $U_j$, where $R_{P,j}=[EP_{T,j}(P)-EP_{T,S}]/[EP_{T,N}-EP_{T,S}]$. In addition, the ratio $R_{P,j}$ further determines a predicted remaining usage $(R_{P,j} \Delta U_F)$ which is equivalent to the second measured remaining usage from the second measurement.

It will be appreciated that the predicted ratio $R_{P,j}$ is smaller than the first predicted ratio at the first usage $U_i$, $R_{P,i}=[EP_{T,i}(P)-EP_{T,S}]/[EP_{T,N}-EP_{T,S}]$. This results in that the predicted remaining usage $(R_{P,i}\Delta U_F)$ is also less than the first predicted remaining usage $(R_{P,i} \Delta U_F)$. However, the first predicted remaining usage $(R_{P,i} \Delta U_F)$ is predicted for the oil in the normal deterioration where there is the absence of water in the oil. Therefore, it can conclude that an abnormal deterioration of the oil is due to the water presence, where the second measured remaining usage will be less than the first predicted remaining usage $(R_{P,i} \Delta U_F)$ relative to the same first actual usage. It will be appreciated that the above disclosure is a general conclusion, which serves as prediction of presenting water in the oil for any situations, as long as the sensing capacitor which is fully immersed in the mixture of water and oil.

Thus, the present invention continually has the following steps to conclude the normal and abnormal deterioration of the oil which occurs in the respective absence and presence of water after the prior step (k):

(l) repeating steps (f) and (g) from a second measurement to obtain a second measured temperature compensated electrical property of the sensing capacitor which represents a second temperature compensated electrical property of the oil according to the first actual usage, from which obtaining a second measured remaining usage ratio and second measured remaining usage;

(m) determining a normal deterioration of the oil which occurs in the absence of water if the second measured remaining usage is similar to the first predicated remaining usage $(R_{P,i}\Delta U_F)$, and confirming the second measured remaining usage which represents a remaining actual usage of the oil;

(n) determining an abnormal deterioration of the oil which occurs in the presence of water if the second measured remaining usage is less than the first predicated remaining usage $(R_{P,i}\Delta U_F)$.

It will be appreciated that the step (m) is based on the previous conclusion of a normal deterioration of the oil which occurs in the absence of water if the first measured remaining usage $(R_{M,i}\Delta U_F)$ is similar to the first predicated remaining usage $(R_{P,i}\Delta U_F)$. The step (m) is also reasonable since all of the measured remaining usages will be similar to the first predicted remaining usage $(R_{P,i}\Delta U_F)$ for the oil being free of water if multiple times of measurement are conducted at the same actual usage of the oil.

Besides the above disclosed method which compares the second measured remaining usage with the first predicted remaining usage to conclude the presence of water in the oil, there is an alternative way in use of an actual remaining usage, which can also reach the same conclusion.

Referring to FIG. 15, there is illustrated that the second measured property $EP_{T,i,w}(M)$ at the first usage $U_i$ due to the water presence is equal to the predicted property $EP_{T,j}(P)$ at the usage $U_j$. Therefore, a second measured remaining actual usage for the oil mixed with the constant small amount of water is equal to $\Delta U_{M2}=(U_S-U_{M2})=(U_S-U_j)$, wherein the usage $U_{M2}$ is the second measured actual usage of the oil which is corresponding to the second measured property $EP_{T,i,w}(M)$ so that $U_{M2}$ is equivalent to $U_j$. As a comparison, the first predicted property $EP_{T,i}(P)$ represents the normal oil deterioration at the usage $U_i$, and a first predicted remaining actual usage for the oil without the constant small amount of water is equal to $\Delta U_P=(U_S-U_P)=(U_S-U_i)$.

Apparently the value of the $\Delta U_{M2}$ is less than the value of the $\Delta U_P$, which also leads to the same conclusion of the abnormal deterioration of the oil which occurs in the presence of water if the second measured remaining actual usage is less than the first predicated remaining actual usage. In contrast, referring to FIG. 15 again it can be easily understood that a normal deterioration of the oil can be concluded from a consistency of the measured and predicted remaining actual usages if it is either according to the first measurement or according to the second measurement at the first usage $U_i$. It will be appreciated that the above analysis is particularly appropriate to the situation having the non-linear relationship between the properties and usages.

In addition, the present invention can detect a likely presence of water in the oil as below, which applies the second measured temperature compensated electrical property:

observing a likely presence of water in the oil 22 if the following occur:

the second measured temperature compensated electrical property exhibits a sudden change which indicates extra deterioration of the oil than deterioration predicted by the first predicted property $EP_{T,i}(P)$; and the second measured temperature compensated electrical property has a value which differs from the first predicted property $EP_{T,i}(P)$, wherein the difference indicates extra deterioration of the oil than deterioration predicted by the first predicted property.

Figure 17:
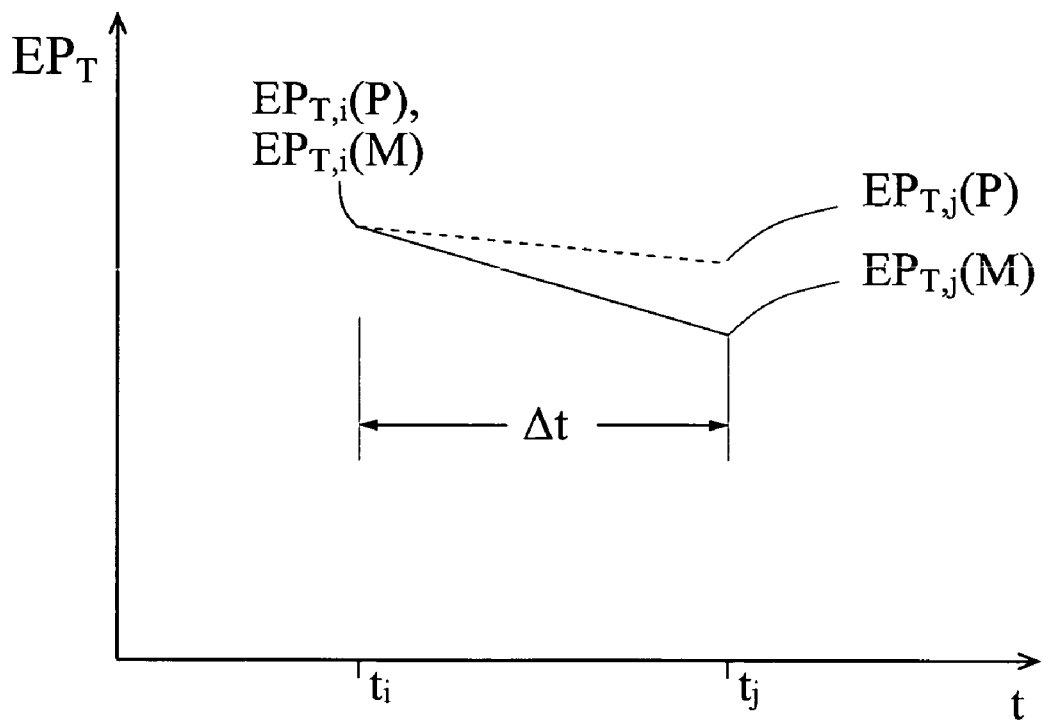
FIG. 17 is a graph which shows that a profile of measured temperature compensated electrical properties during the time period of $t_i$ and $t_j$ has a steeper slope than a slope of the predicated property profile.

Now referring to FIG. 17, there is illustrated another embodiment of the present invention applying the property $(EP_T)$ for detecting the abnormal oil deterioration which occurs in the presence of water.

FIG. 17 illustrates an event happened during a period of the used times $\Delta t=(t_j-t_i)$, wherein $t_i$ is a first usage of time and $t_j$ is a second usage of time. The event causes inconsistency of the respective measured and predicted property profiles, including that a second measured property $EP_{T,j}(M)$ is smaller than a second predicted property $EP_{T,j}(P)$ relative to the same second usage of time $t_j$. This contradicts that the respective first measured and predicted properties $EP_{T,i}(M)$ and $EP_{T,i}(P)$ have the same value at the first usage of time $t_i$. In this embodiment, the likely presence of water in the oil can be detected by comparing a rate of change of the measured properties $EP_T(M)$ with a rate of change of the predicted properties $EP_T(P)$, wherein the measured properties $EP_T(M)$ of the oil exhibit a faster rate towards the oil deterioration. Obviously, the rate is expressed as $\Delta EP_T/\Delta t$. Therefore, the faster rate from the measured properties indicates extra deterioration of the oil than the oil deterioration predicted by the predicted properties.

It will be appreciated that an increased water amount in the oil over the time is the most likely reason to cause the above illustrated phenomenon. This could be happened if the rupture of the head gasket is big enough, which allows a large amount of water to enter into the oil system so that the dynamic water balance in the oil cannot be maintained, as compared with the condition illustrated in FIG. 16.

It will be further appreciated that, if in the absence of water in the oil, the second usage of the time $t_j$ can be determined according to a second measured temperature compensated electrical property which is compared with the second predicted property from the profile of the predicted properties $EP_T(P)$. However, regarding the situation that water presents during the period of the used times $\Delta t=(t_j-t_i)$, there is a need of a second calibration means for counting the elapsed usages including the used times $\Delta t$ according to the first usage of the time $t_i$. Therefore the second usage of the time $t_j$ can be defined, from which it can further define the second predicted property $EP_{T,j}(P)$ to thereby claim the conclusions that are disclosed in FIG. 17. The second calibration means includes a sensor of counting a number of turns of a wheel of a vehicle or a crank of an engine as counting the elapsed usages of miles, or a digital time clock of a microprocessor in the vehicle for counting times including times of outputting electricity from a generator of the engine as counting the elapsed usages of times.

Figure 18:
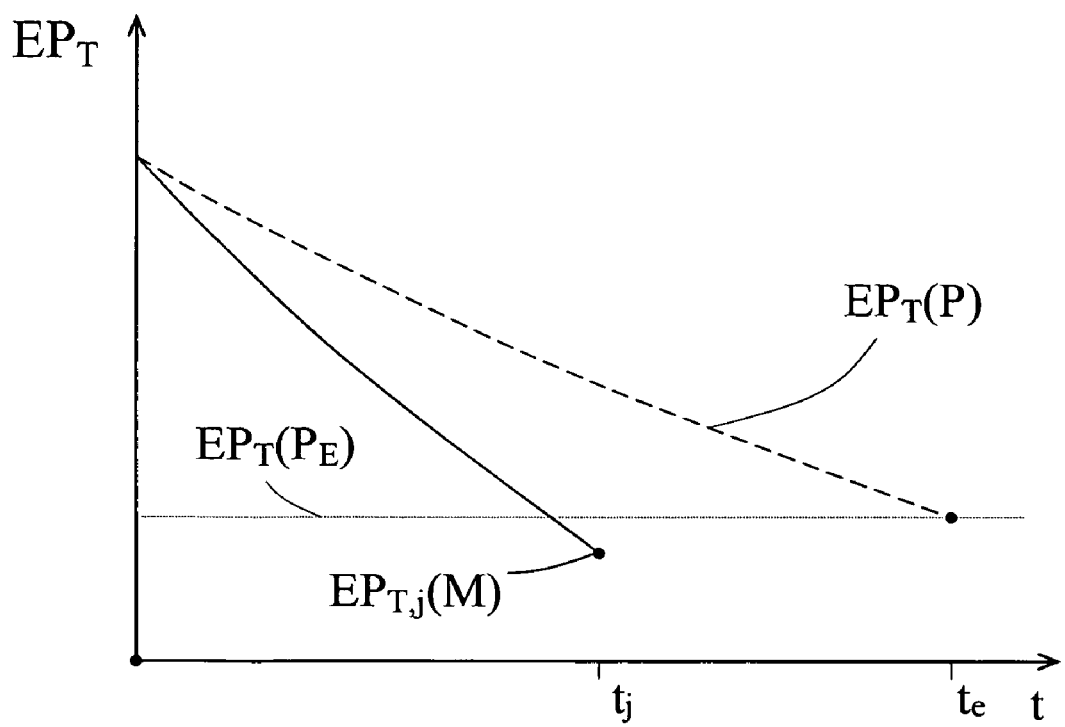
FIG. 18 is a graph showing a measured temperature compensated electrical property profile which exceeds a predetermined extreme value of the predicted temperature compensated electrical property before it should be.

In addition to situations which are illustrated in FIGS. 16 and 17, FIG. 18 illustrates an additional situation where water could be in the oil. Referring to FIG. 18, the measured and predicted property profiles have a common value at a very beginning. However, there is illustrated second measured property $EP_{T,j}(M)$ at a second usage of time $t_j$, which exceeds a predetermined extreme value of the predicted property $EP_T$ ($P_E$) at an usage of time $t_e$ from the profile of the predicted properties $EP_T(P)$. In addition, the second measured property $EP_{T,j}(M)$ exceeds the predetermined extreme value at the second usage of time $t_j$ which is earlier than the predicted usage of time $t_e$: $(t_j<t_e)$. Of course earlier could be earlier in times, earlier in miles, etc. This too is an indication of presence of water in the oil.

Therefore, according to the illustrations of FIGS. 17 and 18 the present invention for detecting the likely presence of water in the oil comprise the claims as bellow:

observing a likely presence of water in the oil 22 if any of the following occur:

the first and second measured temperature compensated electrical properties related to the respective first and second actual usages of the oil has a rate of change of deterioration of the oil which differs from a rate of change of deterioration determined by the first and second predicted properties related to the respective first and second actual usage, wherein the difference indicates extra deterioration of the oil than deterioration predicted by the first and second predicted properties; and the second measured temperature compensated electrical property at a second actual usage of the oil has a value which exceeds a predetermined extreme value of the predicted property profile, wherein the predetermined extreme value is exceeded at the second usage which is earlier than an actual usage predicted by the predicted property profile.

Figure 19:
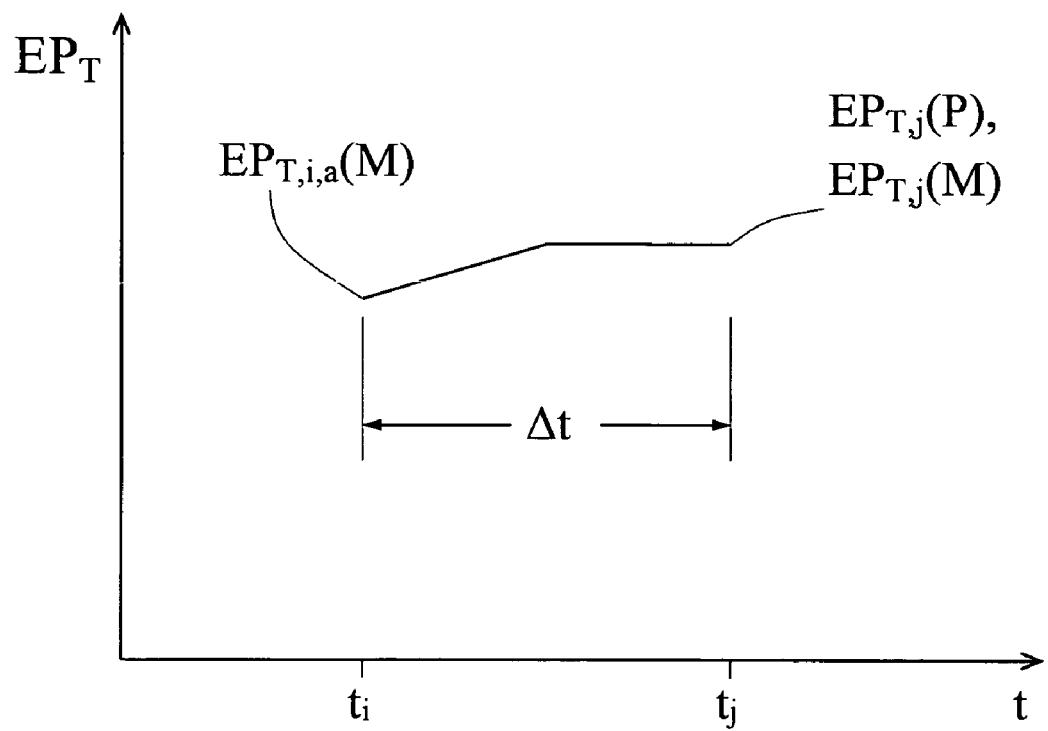
FIG. 19 is a graph showing a profile of measured temperature compensated electrical properties in a cold internal combustion engine which exhibits an initial anomaly of extra oil deterioration.

Reference to FIG. 19 illustrates a first measured temperature compensated electrical property which exhibits an initial anomaly $EP_{T,i,a}(M)$ according to a first moment $t_i$, and then returns to a value of a second predicted property $EP_{T,j}(P)$ at a second moment $t_j$. This can occur in a first few minutes $\Delta t$ after a cold internal combustion engine is started, wherein water has condensed into the oil before the engine is started. The presence of the condensed water causes the impedance or voltage have a value which is less than anticipated. However, after the engine has run for a short period of time, the condensed water evaporates and a second measured property $EP_{T,j}(M)$ returns to a nominal value of the second predicted property $EP_{T,j}(P)$.

In this fashion an additional embodiment for detecting the presence of water in the oil, comprises;

in step (a), providing an oil disposed in a crankcase of a cold internal combustion engine; starting the engine; observing a likely presence of the condensed water in the oil if a first measured temperature compensated electrical property exhibits an initial anomaly, which indicates extra deterioration of the oil.

The illustrations from FIGS. 16, 17, 18 and 19 disclose the abnormal oil deterioration according to an impedance or a voltage measurement. It will be appreciated that if using a current measurement, curves corresponding to the abnormal oil deterioration can be derived according to the base curve in FIG. 8.

The above discloses the first preferred embodiment of the present invention methods, which applies a dual sensor configuration including the sensing capacitive sensor immersed in the oil, and the referencing capacitive sensor immersed in the reference oil to obtain the measured temperature compensated electrical properties of the oil. Applying the dural sensor strategy the present invention enables to quantitatively obtain the measured remaining usage of the oil as $(R_M \Delta U_F)$ or $\Delta U_M$. From using the measured remaining usage of the oil, the present invention further enables to differentiate the oil deterioration which occurs in the presence or absence of water.

Figure 23:
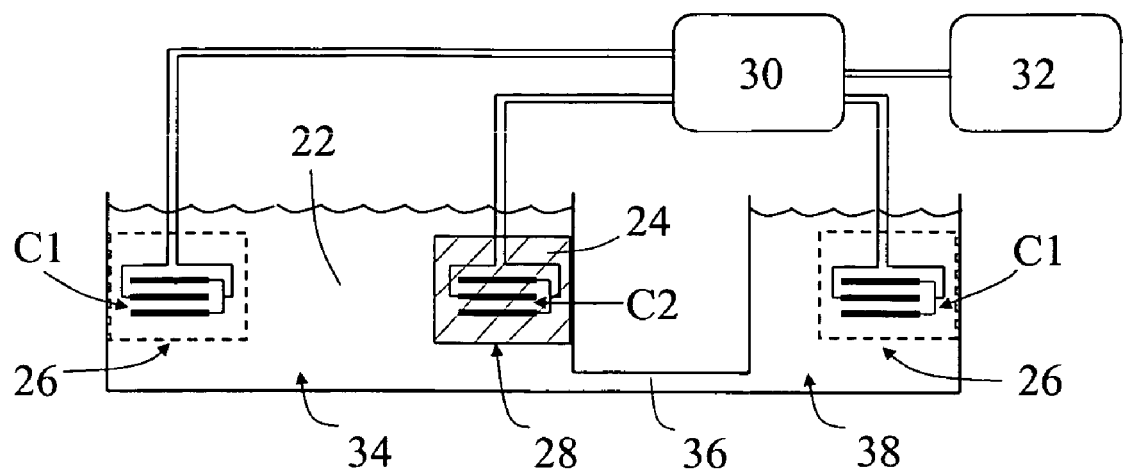
FIG. 23 is a diagram of an apparatus from a variation of the first preferred embodiment of the present invention, which applies at least two measurement sensors having the respective at least two sensing capacitive sensors positioned at the respective different locations of an oil system.

A variation of the above disclosed first preferred embodiment is comprised of at least two measurement sensors including first and second of the respective at least two measurement sensors as illustrated in FIG. 23. They can be affixed into specific locations of an entire lubricating oil system, such as the system of a locomotive diesel engine or ship diesel engine having a separated crankcase 34 as a first location and lubricating oil reservoir 38 as a second location which are connected by oil transporting lines 36. Therefore, the varied embodiment enables to in-situ monitor if an uneven distribution of the oil deterioration occurs through the system, particularly for detecting if there would be water accumulated in the specific locations of the system.

In this embodiment of the variation as illustrated in FIG. 23, each of the first and second of the respective at least two measurement sensors can be paired with one individual reference sensor, or the first and second of the respective at least two measurement sensors are combined with the same reference sensor as shown in FIG. 23. Analogy with the disclosed embodiment according to including FIGS. 9-11, both options enable to generate the respective two second remaining usages of the oil according to the specific locations where the first and second of the respective at least two measurement sensors are positioned. Therefore, comparing these two second remaining usages of the oil with the first predicted remaining usage for the oil, it can conclude (1) an even distribution of the normal oil deterioration in the oil system if the two second measured remaining usages of the oil are similar as compared with the first predicted remaining usage for the oil, and (2) an uneven distribution of the oil deterioration in the oil system if the two second measured remaining usages of the oil are dissimilar from each other as compared with the first predicted remaining usage for the oil.

It will be appreciated that, in that situation (2), a further analysis can be conducted on differences including among the two second measured remaining usages and from different combinations of the first predicted and one of the two second measured remaining usages. Therefore, an identification of the uneven distribution in the entire oil system is readily available and understood in accordance with the spirit and scope of the present invention methods. Therefore, such detailed analyses will not be repeated.

Figure 20:
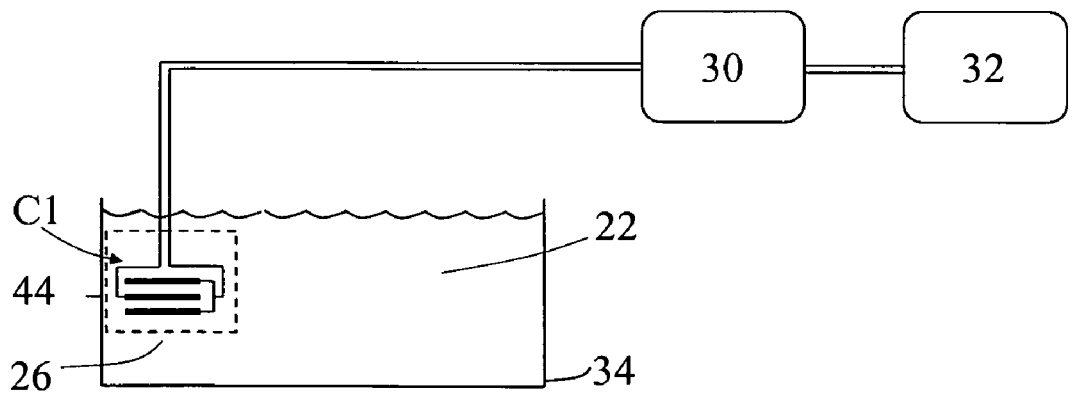
FIG. 20 is a diagram of a second apparatus of the present invention, which only applies the measurement sensor for detecting the oil deterioration and oil level.

Now referring to FIG. 20, there is illustrated a diagram of a second apparatus for detecting deterioration in oil from the present invention. This apparatus measures a property of the sensing capacitive sensor C1 of the measurement sensor 26 to represent a measured temperature compensated electrical property $EP_T(M)$ of the oil 22. The measured property $EP_T(M)$ is temperature compensated according to the aforementioned method, or any other desired methods, such as actually measuring the temperature of the oil and applying a compensation factor to the measured property. Correspondingly, the method of the second preferred embodiment for obtaining the temperature compensated electrical property of the oil is claimed as follows:

(a) providing an oil 22 in use which is known not to contain water, the oil is disposed in an oil system of a machine such as a crankcase of an engine or a container of an electrical transformer;

(b) providing a measurement sensor 26 which includes a sensing capacitive sensor C1;

(c) positioning the sensor 26 to the oil system, wherein said sensor C1 is immersed in the oil;

(d) using a measuring device for measuring a first measured temperature compensated electrical property of the sensing capacitive sensor C1 from a first measurement, which represents a first temperature compensated electrical property $EP_{T,i}(M)$ of the oil, wherein the measured property of the sensor is one of:

the impedance of the sensing capacitive sensor C1;

the current passing through the sensing capacitive sensor C1;

the voltage developed across the sensing capacitive sensor C1;

In addition, following the above disclosed procedures which are used for obtaining the measured temperature compensated electrical property of the oil in step (d), the second embodiment of the present invention further comprises a step (e):

(e) establishing a predicted temperature compensated electrical property profile for the oil, which represents the normal deterioration of the oil, the predicted temperature compensated property profile includes a property $EP_{T,N}$, which is equal to a measured property $EP_T(M)$ of the oil if it is unused or new and dry, and another property $EP_{T,S}$, which is equal to a measured property $EP_T(M)$ of the oil if it is spent and dry.

Once after establishing the profile of the predicted properties $EP_T(P)$, the second preferred embodiment of the present invention can apply all the same strategies thus the same elements of the first preferred embodiment, including a second measurement, and a comparison of the second measured remaining usage and remaining actual usage in the respective two forms (R$\Delta$U) and $\Delta$U with the respective first predicted remaining usage ($R_{P,i}\Delta U_F$) and predicted remaining actual usage.

The comparison can conclude deterioration of the oil which occurs in the presence or absence of water and further confirm the second measured remaining usage which represents the remaining actual usage of the oil in the normal deterioration of the oil, in addition to obtain the deterioration ratio $D_M$ of the oil. Further it will be appreciated that, the second embodiment of the present invention can incorporate with the illustrations of FIGS. 16, 17, 18 and 19 for various situations where the oil deteriorates in the presence of water. However, for a purpose to reduce the length of this application, all of the same strategies, which have been disclosed in the first preferred embodiment, will not be repeated for the disclosure of the second preferred embodiment.

It will be further appreciated that the resistance and capacitive reactance are also appropriate for the second embodiment according to the spirit and scope of the present invention.

It will be another appreciated that the second preferred embodiment further enables to comprise at least two measurement sensors, as illustrated in FIG. 23 for the first preferred embodiment, for monitoring if there is uneven distribution of the oil deterioration through the entire lubricating oil system of the machine.

II. Method for Detecting Level of an Oil

It is well known that during operation of a machine such as the internal combustion engine, lubricating oil in use will be consumed over usages which causes amount of the oil disposed in the oil system of the machine is reduced, so as to lower a top level of the oil in the oil system. When the oil amount is reduced to be lower than a predetermined threshold amount which is usually defined by a manufacturer of the machine, moving parts of the machine can not be effectively protected. Therefore, it is necessary to have a method which can on-line detect a top level of the oil in use which is reduced to the top level of a threshold amount of the oil for protecting the machine when the oil is consumed.

As in the case illustrated in FIG. 9 when the measurement sensor 26 is installed on the upward wall of the crankcase 34 of the internal combustion engine, the sensing capacitive sensor C1 is immersed in the oil 22 and is aligned with a position 44 which correlates to the top level of the predetermined threshold amount of the oil. Therefore, reduction of amount of the oil will lower the top level of the oil in the crankcase. When the top oil level is reduced to the top level of the threshold amount of the oil, it will cause the sensing capacitive sensor C1 that is not fully immersed in the oil, where its lower part is immersed in the oil and upper part is filled with the air. The fact that the sensing capacitive sensor C1 is partially immersed in the oil will cause a change of the electrical property of the sensor, as compared with the property when the sensor is fully immersed in the oil. Therefore, this situation provides the present invention an opportunity to detect the top oil levels including a top level of the predetermined threshold amount of the oil by detecting abnormal electrical properties of at least two measurement sensors, which are installed according to the respective levels of the oil.

The following first illustrates a method of the present invention for detecting the top level of the threshold amount of the oil from applying the single measurement sensor, which is illustrated in FIG. 9. The method is still based on the strategy of comparing the measured remaining usage of the oil with the predicted remaining usage for the oil.

It is well known that a plate capacitor C including two plates in parallel has a capacitance described as $C_P = \in S/d$, wherein $\in$ is the dielectric constant of a dielectric medium of the capacitor, S is an effective area of the plates, and d is a distance between the plates.

Now comparing a capacitance $C_P$ of the capacitor in two conditions, (1) if it is filled with a first dielectric medium with a dielectric constant $\in_1$, and (2) if it is filled with a second dielectric medium with a dielectric constant $\in_2$, it can conclude that a difference between their capacitances $C_{P1}$ and $C_{P2}$ is proportional to the difference of the constants $\in_1$ and $\in_2$.

According to the above defined conditions of the capacitances $C_{P1}$ and $C_{P2}$ for the same capacitor, in addition to a fact that the dielectric constant $\in(a)$ of the air is substantially less (approximately 2-3 times) than the dielectric constant $\in(o)$ of the oil including the mineral oil and silicon oil (this information can be found elsewhere including from the website: clippercontrol having a ".com" suffix), therefore, the capacitance $C_{P2}$ of the capacitor filled with the air is less than the capacitance $C_{P1}$ of the same capacitor filled with the oil. It can further conclude that, the impedance $Z_2$ of the capacitor filled with the air is bigger than the impedance $Z_1$ of the same capacitor filled with the oil, the voltage $V_2$ is also bigger than the voltage $V_1$ if the constant current measurement is applied, and the current $I_2$ is smaller than the current $I_1$ if a constant voltage measurement is applied.

Now comparing a capacitance $C_P$ of the capacitor in another two situations, (1) a part of the capacitor is filled with the air and the rest of the capacitor is filled with the oil, and (2) the same capacitor is fully filled with the oil.

In the first situation when the part of the capacitor is filled with air and the rest part is filled with oil, the capacitance $C_{P1}$ is a summation of a capacitance of the air: $C_{P1}(a)=\in(a) S_a/d$ and a capacitance of the oil: $C_{P1}(o)=\in(o)S_o/d$, wherein $S_a$ is an effective plate area which is occupied by the air, and $S_o$ is the area which is occupied by the oil, and $S=(S_a+S_o)$.

If comparing the capacitance $C_{P1}$ of the capacitor filled with the air and oil in the first situation with the capacitance $C_{P2}$ of the same capacitor fully filled with the oil in the second situation, a ratio of $C_{P1}/C_{P2}$ is equal to $[\in(a) S_a/d+\in(o)S_o/d]/\in(o)S/d$. The ratio can be simplified as: $C_{P1}/C_{P2}=[\in(a)S_a+\in(o)S_o]/\in(o)S$. Through a mathematic transformation, the simplified ratio is equal to: $1-[\in(o)-\in(a)] S_a/S$, which has a value of less than a unity 1.

The above analysis states that the capacitance $C_{P1}$ of the capacitor whose a part filled with the air and the rest filled with the oil is less than the capacitance $C_{P2}$ of the same capacitor which is fully filled with the oil.

It will be appreciated that, from the above conclusion, one can derive that the impedance $Z_1$ of the capacitor having the capacitance $C_{P1}$ is bigger than the impedance $Z_2$ of the same capacitor having the capacitance $C_{P2}$. Accordingly, the voltage $V_1$ is higher than the voltage $V_2$ if applying a constant current measurement, and the current $I_1$ is smaller than the current $I_2$ if applying a constant voltage measurement. Therefore, the electrical property of the capacitor filled with the oil and air will provide a false phenomenon less deterioration of the oil, as compared with the oil deterioration determined by the same capacitor which is fully filled with the oil.

It will be further appreciated that conclusions that are the same as the above statements can be rationalized in application of the sensing capacitive sensor. However, instead of providing a rationalization in a similar fashion, the present invention demonstrates experimental results listed at the end of this disclosure, which are consistent with the conclusion of the rationalization.

Figure 21:
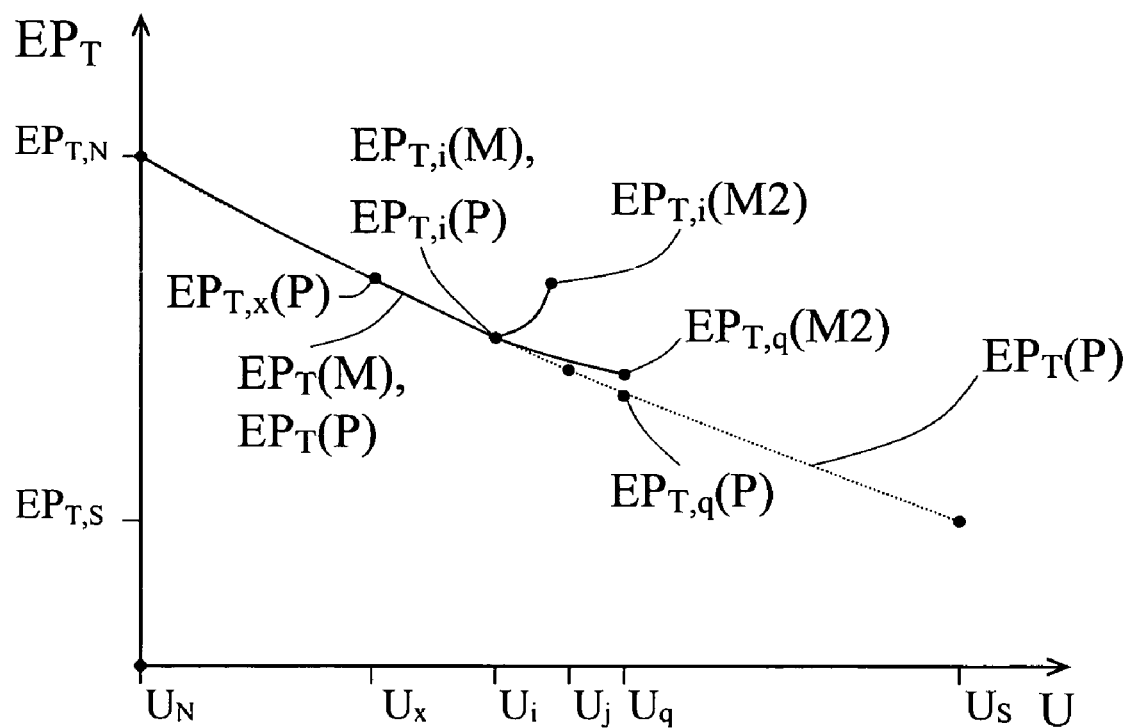
FIG. 21 is a graph which shows the same curves in FIG. 14. The difference in FIG. 21 is that the measured properties starting from the usage $U_i$ are different from the predicted properties, which indicates less oil deterioration than it should be.
Figure 22:
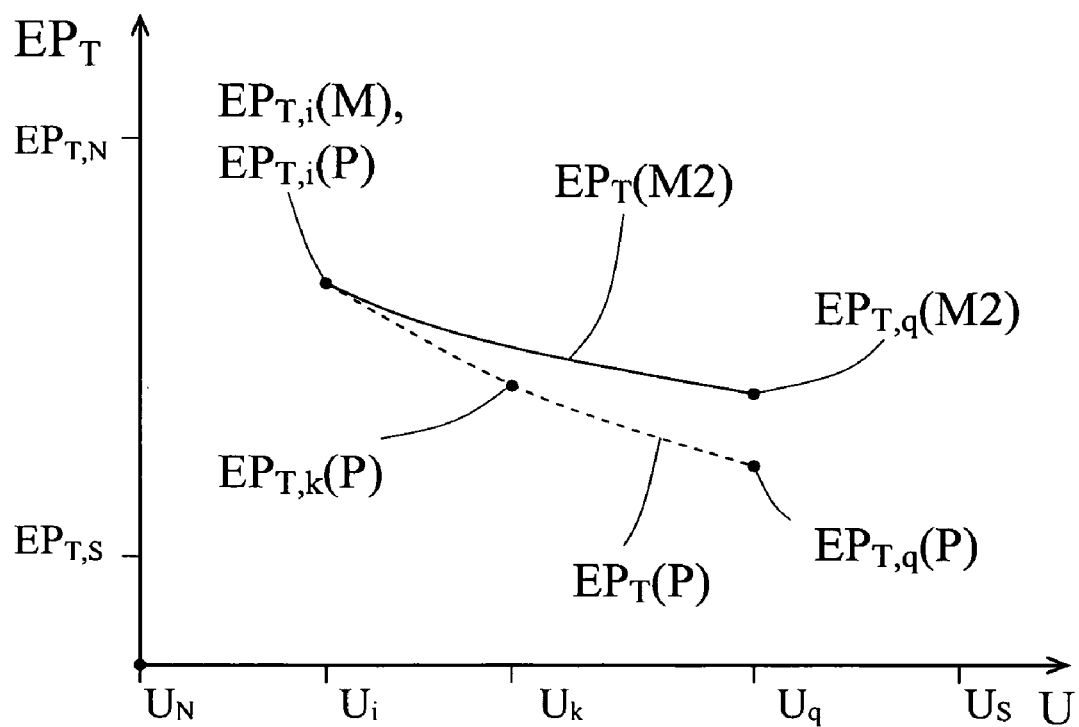
FIG. 22 is a graph which magnifies sections of the respective measured and predicted property profiles related to a range of usages from the usage $U_i$ to the usage $U_q$ of FIG. 21 according to a first situation of losing oil.

Having the above conclusions in mind and referring to FIGS. 21 and 22 now, there is illustrated how reduction of the oil to its threshold amount causes a change of the measured temperature compensated electrical property and the remaining usage of the oil as well from the present invention. FIG. 21 illustrates a partial profile of the measured properties $EP_T(M)$, and a profile of the predicted properties $EP_T(P)$ which includes the respective properties $EP_{T,N}$ and $EP_{T,S}$ to correspond the respective usages $U_N$ and $U_S$. The predicted property profile is the same one as that illustrated in FIG. 14.

As illustrated, up to the first actual usage $U_i$ the first measured property $EP_{T,i}(M)$ is consistent with the first predicted property $EP_{T,i}(P)$. However, staring from the first usage $U_i$, the measured property differs from the predicted property due to the amount of the oil which is reduced to the threshold amount. Therefore, a top level of the oil is lowered to reach the top level of the predetermined threshold amount of the oil, which is aligned with the position 44, as illustrated in FIG. 9. In this situation, an upper part of the sensing capacitive sensor C1 is filled with the air.

It will be appreciated that there are various situations which cause the sensing capacitive sensor that is not fully immersed in the oil. However they can be always classified to a first situation: (1) a gradually losing the oil, such as extra consumption of the oil according to an intensive usage of the machine, and a second situation: (2) a significantly losing the oil in a short period of the time, such as an oil leaking of the crankcase. Referring to FIG. 21, there are illustrated second measured properties $EP_{T,q}(M2)$ and $EP_{T,i}(M2)$ according to the respective described first and second situations (1) and (2).

As illustrated in FIG. 21, in the first situation of the gradually losing the oil, the second measured property $EP_{T,q}(M2)$ behaves a correspondingly gradual departure from the profile of the predicted properties $EP_T(P)$. For example an impedance or a voltage of the sensing capacitive sensor is increasingly larger than the corresponding predicted value. In contrast, in the second situation of the quickly losing the oil, the second measured property $EP_{T,i}(M2)$ exhibits a sudden change during a small interval of the first usage $U_i$. Accordingly, the sensing capacitive sensor also suffers a significant loss of the oil, which makes the measured property change dramatically towards a direction of less oil deterioration. For example, the impedance or voltage exhibits a sudden and dramatic increase of the value. It will be appreciated that the first situation (1) represents the most probable situations, where occur that a top level of the oil is reduced to the top level of the predetermined threshold amount of the oil. Thus, FIG. 22 particularly illustrates the situation, from which a conclusion can be conducted for determining the predetermined threshold amount of the oil from detecting the corresponding top oil level. This conclusion can also be applied to the second situation (2).

FIG. 22 magnifies a part of the profiles in FIG. 21 starting a first measured property $EP_{T,i}(M)$ at the first usage $U_i$ from a first measurement, when the measured property $EP_T(M2)$ departs from the predicted one. After spending a short range of usages from the first usage $U_i$ to a second usage $U_q$, the measured property exhibits a value of the second measured property $EP_{T,q}(M2)$ at the second usage $U_q$ from a second measurement, which is larger than a value of a second predicted property $EP_{T,q}(P)$ representing a normal consumption of the oil according to the second usage $U_q$. Moreover, in this situation a value of the second measured property $EP_{T,q}(M2)$ is equal to a value of a predicted property $EP_{T,k}(P)$ which correlates to an usage $U_k$. Obviously, the usage $U_k$ happens earlier than the second usage $U_q$.

Therefore, the second measured property at the second usage $U_q$ from the second measurement has a second measured remaining usage ratio, which is equal to a predicted remaining usage ratio at the usage $U_k$: $R_{P,k}=[EP_{T,k}(P)-EP_{T,S}]/[EP_{T,N}-EP_{T,S}]$. The usage ratio $R_{P,k}$ further determines the remaining usage $(R_{P,k}\Delta U_F)=R_{P,k}\times(U_S-U_N)$. Thus, the second measured remaining usage according to the second measured property $EP_{T,q}(M2)$ is equal to the predicted remaining usage $(R_{P,k}\Delta U_F)$.

Apparently, the predicted remaining usage ratio $R_{P,k}$ is larger than a second predicted remaining usage ratio: $R_{P,q}=[EP_{T,q}(P)-EP_{T,S}]/[EP_{T,N}-EP_{T,S}]$, where the ratio $R_{P,q}$ correlates to the physical condition having a sufficient amount of the oil that is dry in the oil reservoir, which makes the sensing capacitive sensor C1 fully immersed in the oil. This situation also results in that the predicted remaining usage $(R_{P,k}\Delta U_F)$ is larger than a second predicted remaining usage $(R_{P,q}\Delta U_F)$. Therefore, the above analysis concludes: the second measured remaining usage which is equivalent to $(R_{P,k}\Delta U_F)$ is apparently larger than the second predicted remaining usage $(R_{P,q}\Delta U_F)$, wherein the second predicted remaining usage represents the situation that the sensing capacitive sensor is fully immersed in the oil whose amount is sufficient so that a top oil level is higher than the level of the predetermined threshold amount of the oil.

Consequently, a conclusion can be made according to the first situation: determining a top level of the oil which is reduced to the top level of a predetermined threshold amount of the oil if the second measured remaining usage related to the second actual usage is larger than the second predicted remaining usage according to the same second actual usage. It will be appreciated that the above is a general conclusion for all situations including the situation (2) where the insufficient amount of the oil also happens. In addition, for reaching the conclusion of this situation, the second calibration means is needed, which defines the second actual usage $U_q$.

It will be further appreciated that, there is an alternative way which can conduct the same conclusion regarding the first situation. Referring to FIGS. 21 and 22, there is illustrated that the second actual usage $U_q$ corresponds to the second predicted property $EP_{T,q}(P)$. Therefore, the second predicted remaining actual usage is $\Delta U_{P2}=\Delta U_q=(U_S-U_{P2})=(U_S-U_q)$, wherein $U_{P2}$ is a second predicted actual usage according to the second predicted property. However, the second measured property $EP_{T,q}(M2)$ is equal to the predicted property $EP_{T,k}(P)$, which corresponds to the actual usage $U_k$ that is equivalent to the second actual usage $U_{M2}$ of the second measured property $EP_{T,q}(M2)$. Thus, the second measured remaining actual usage $\Delta U_{M2}=(U_S-U_{M2})$ is equivalent to the predicted remaining actual usage $\Delta U_k=(U_S-U_k)$, wherein $U_{M2}$ is a second measured actual usage in accordance with the second measured property. Apparently, the second measured remaining actual usage $\Delta U_{M2}$ is larger than the second predicated remaining actual usage $\Delta U_{P2}$. This leads to the above illustrated same conclusion of reaching the top level of the threshold amount of the oil during the oil reduction. Therefore, despite of shapes of the temperature compensated electrical property profiles, the embodiment of the present invention enables to diagnose if it reaches the top level of the threshold amount of the oil during aggravation of the oil reduction.

In addition to application of the remaining usage of the oil, the second measured temperature compensated electrical property also can be used to predict that the top oil level is reduced to the top level of the threshold amount of the oil according to the illustrations of FIGS. 21 and 22. As illustrated in the case of the first situation (1), the second measured property $EP_{T,q}(M2)$ differs from the second predicted property $EP_{T,q}(P)$. However, their difference indicates less oil deterioration determined by the second measured property $EP_{T,q}(M2)$ as compared with deterioration determined by the second predicted property $EP_{T,q}(P)$. Therefore, the present invention can further conclude as follows for the first situation:

predicting a top level of the oil which is reduced to the top level of the predetermined threshold amount of the oil if the second measured temperature compensated electrical property differs from the second predicted temperature compensated electrical property wherein the difference indicates less deterioration of the oil determined by the second measured temperature compensated electrical property than deterioration determined by the second predicted temperature compensated electrical properties.

Referring to FIG. 21 regarding the second situation of dramatically losing the oil, the second measured property $EP_{T,i}(M2)$ is equivalent to a predicated property $EP_{T,x}(P)$ which correlates to an actual usage $U_x$. Therefore, a second measured remaining usage according to the second measured property $EP_{T,i}(M2)$ is equivalent to $(R_{P,x}\Delta U_F)$, which is apparently larger than a first predicted remaining usage $(R_{P,i}\Delta U_F)$ predicted by the first predicted property $EP_{T,i}(P)$. In addition, a second measured remaining actual usage $\Delta U_{M2}$ according to the second measured property $EP_{T,i}(M2)$ is equivalent to $(U_s-U_{M2})=(U_s-U_x)$, which is also apparently larger than a first predicted remaining actual usage $-\Delta U_P-(U_s-U_P)=(U_s-U_i)$ that is predicted by the first predicted property $EP_{T,i}(P)$.

From the above analysis, it can conclude a top level of the oil which is reduced to the top level of the predetermined threshold amount of the oil according to the respective judgements: (i) the second measured remaining usage is larger than the first predicted remaining usage; (ii) the second measured remaining actual usage is larger than the first predicted remaining actual usage; and (iii) the second measured temperature compensated electrical property differs from the first predicted temperature compensated electrical property wherein the difference indicates less deterioration of the oil determined by the second measured temperature electrical property than deterioration predicted by the first predicted temperature compensated electrical property.

It will be appreciated that the illustrated curves for the electrical property in FIGS. 21 and 22 is one of the impedance or voltage. If the measured property is the current, the curve would be as that shown in FIG. 8. In addition, the electrical property could be one of the components of the impedance, resistance or reactance, rather than the total composite impedance.

Figure 24:
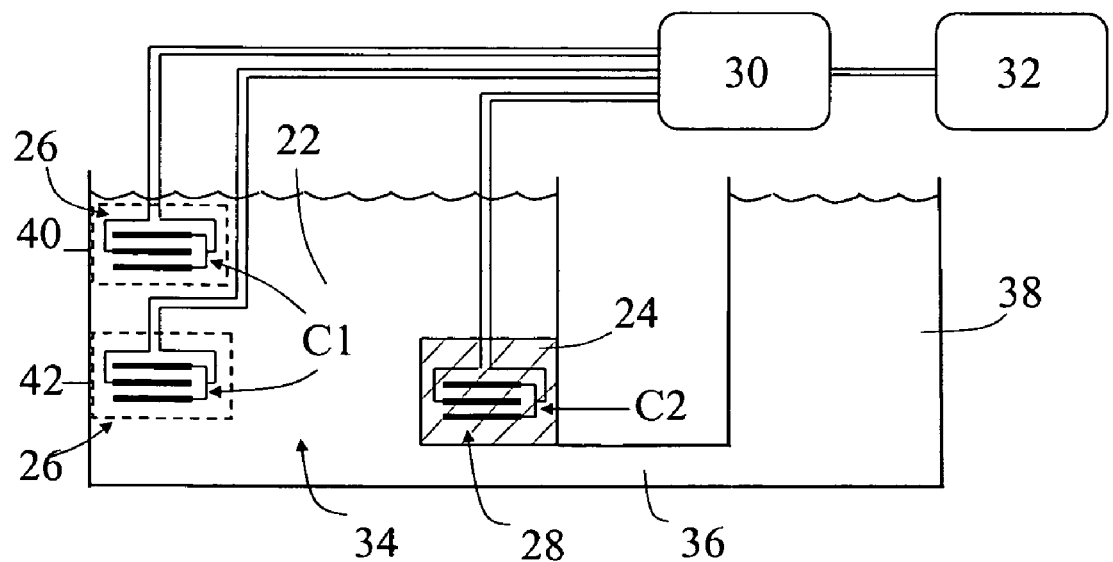
FIG. 24 is a diagram of an apparatus from another variation of the first preferred embodiment of the present invention applying at least two measurement sensor, wherein at least two sensing capacitive sensors are positioned onto the respective different levels of an oil system.

Referring to FIG. 24, a variation of the above disclosed embodiment is to apply at least two measurement sensors 26 positioned along a vertical orientation to monitor change of a full scale of the top level of the oil in the crankcase 34. For example, in this embodiment, the first of the at least two measurement sensors is positioned onto the upward wall of the oil reservoir 34, wherein its sensing capacitive sensor is aligned with a position 40. The position is adjacent to but below the initial top level of the oil when a full amount of the oil is just newly disposed in the oil reservoir. The second of the at least two measurement sensors is installed wherein its sensing capacitive sensor is positioned to align with the top level 42 of the threshold amount of the oil.

Therefore, the sensing capacitive sensor of each of the respective first and second of the at least two measurement sensors will provide a respective information on change of the oil level starting an initial top level of the full amount of the oil, which then drops to the level of the threshold amount of the oil. The user of the machine can then take appropriate actions to protect the machine from damage. In addition, a third measurement sensors can also be installed to a level which is lower than the top level of the threshold amount of the oil. In this embodiment, each of the first and second of the respective at least two measurement sensors can be combined with one individual reference sensor, or the first and second of the respective at least two sensors can be combined with the same one reference sensor 28 shown in FIG. 24, or several measurement sensors are combined with a reference sensor. All of these variations are within the spirit and scope of the present invention.

It will be appreciated that the above disclosed embodiment for predicting the top level of the threshold amount of the oil can also be applied to the second preferred embodiment illustrated in FIG. 20, where the sensing capacitive sensor C1 is aligned with the top level 44 of the threshold amount of the oil. It will be additionally appreciated that the second preferred embodiment also enables to detect change of the oil level from applying at least two measurement sensors, which is identical to the illustration in FIG. 24 for the first preferred embodiment. Therefore, a disclosure of this embodiment will not be repeated again.

It will be further appreciated that there is a very small probability that two events happen simultaneously when a large amount of the water enters into the oil and the oil significantly leaks from the reservoir. Therefore, the present invention excludes discussions of this situation which occurs in the very small probability, and which can also be classified accordingly following the spirit and scope of the present invention.

EXAMPLES

The following are examples and experimental information of the present invention, regarding the capacitive sensor having the integrated plated electrodes operated by an AC voltage of a single frequency to test samples of lubricating oil, which are offered by way of illustration only and not by way of limitation and restriction.

A sensing capacitive sensor was constructed with three identical plates of a copper alloy serving as the respective electrodes. Each metal plate had a thickness of approximately 1 mm and the shape of a table tennis bat, including a bottom rectangular section connected to a top longitudinal bar having a top end serving as the top end of the plate, wherein the bar is aligned with a longitudinal central line of the rectangular section. Obviously the rectangular section provided effective surface areas of the sensor, and the bar served as an electrical connecting means and mechanical supporting means to connect and support the bottom section. Therefore, the bottom section of the plate was not limited to the rectangular shape. In fact, any reasonable shape was appropriate according to spirit and scope of the present invention.

The rectangular section had a width of 15 mm and a length of 30 mm, and a bottom hole positioned on the central line and adjacent to the bottom transverse side of the width. The bar had a length 20 mm, and a top hole positioned at 15 mm to the top end. In addition, there was a mark on the bar which was adjacent to the top transverse side of the width of the rectangular section.

The three plates are positioned upwardly in parallel and alignment with each other to be the respective left, middle and right plates. Two Nylon washers were positioned between left and middle plates, and aligned with the respective bottom and top holes. Similarly, two additional Nylon washers were positioned between middle and right plates, and aligned with the respective bottom and top holes. Each washer had a thickness of approximately 1.5 mm and served as a spacer. In addition, top and bottom Nylon screws were used to penetrate through the respective washers and top and bottom holes of the respective three plates, and were then fastened by the respective two Nylon nuts. Therefore, the capacitive sensor had the same fixed air gap of 1.5 mm between two adjacent plates. The gap was designed including for oil circulation. The screws and nuts were designed for keeping the gap constant when the capacitive sensor was contacted by a circulating oil and affected by vibrations of a running engine. The top ends of the respective left and right plates were electrically connected in parallel by a wire serving as a first electrical pole, and the top end of the middle plate was electrically connected by another wire serving as a second electrical pole.

An AC analyzing device was assembled by application of including an IC chip AB-112 of Wien Bridge Oscillator (Analog Devices, MA USA). After adjustment of electrical parameters, the chip output an AC voltage having 5.40 volts of the root mean square (rms) values at a frequency of 7.25 kHz, which was measured by a Radio Shack digital multimeter (Cat. No.: 22-168A) and verified by an oscilloscope.

Two oil samples were used. The first one was a new oil, and second one was an used oil of being spent for 5000 miles. The following was a procedure to prepare the oil samples. Multiple quarts of commercial oil were purchased and then mixed together to be a pool of the homogeneous oil. A small volume of the homogeneous oil was collected, which served as the sample of the new oil without contamination. Approximately five quarts of the homogeneous oil were poured into the lubricating oil system of a passage car. After the car ran 5000 mils, the oil was collected, and a small portion was used as the sample of the used oil having contaminates according to concepts of the present invention.

A testing circuit was constructed, which was a voltage divider including the sensor connected to a reference impedance of 10 M ohm. Within the circuit, the first electrical pole was connected to the output terminal of the IC chip, and second electrical pole was connected to a first lead of the reference impedance having a second lead that was electrically grounded.

The measurement was conducted by using the multimeter to measure voltages in the rms value across the respective sensor and reference impedance. Therefore, impedance of the sensor was calculated according to the measured voltages.

The testing procedures in order were for measuring the blank electrodes, electrodes filled with the new oil, and electrodes filled with the used oil. When measuring the respective new and used oil, the bottom rectangular section of the sensor was immersed into the respective oil samples, wherein top levels of the respective oil samples were reached to the mark of the sensor. In addition, before testing the sample of the used oil, the electrodes were first washed with the same used oil. Application of these two steps was to minimize the experiment errors.

Test results showed an impedance of 31.0 M Ohm for the blank electrodes of the sensor which was filled with the air, 24.8 M Ohm for the sensor filled with the new oil, and 23.9 M Ohm for the used oil. The testing results were consistent with theories of the higher the dielectric constant of a medium between the electrodes of a sensor, the lower the impedance of the sensor having the corresponding medium. It will be appreciated that, comparing values of the dielectric constants of the respective media in the test, the air of the blank electrodes has the lowest value, the new oil the higher, and the used oil the highest value that was caused in the presence of the contaminates, which were produced in the usage of the oil.

It will be appreciated that, the results of the above disclosed experiment demonstrate that the present invention sensing capacitive sensor can be used to detect deterioration and level of an oil in application of the single frequency of an AC voltage.

An improved sensing capacitive sensor was also studied according to the above disclosed one. The improvement was that multiple openings were drilled on the rectangular section of each plate for increase of the oil circulation. In addition, gaps at top of the bars were filled with epoxy starting from the position of the top Nylon screw to the top end of the respective bars. The purpose was to affix the effective areas of the capacitive sensor which were contacted by an engine oil, when the sensor was positioned into an engine for a test.

Furthermore, in addition to the above disclosed embodiment of the spatial plated electrodes of the sensor, additional embodiments of the respective thick and thin film electrodes are also appropriate for constructing the capacitive sensor of the present invention, wherein the electrodes are positioned onto the respective ceramic and silicon substrates.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A sensor for detecting oil deterioration and oil level, comprising:
   a. a measurement sensor comprising a sensing capacitive sensor that includes left, middle and right identical upward plated electrodes having the respective top and bottom ends, said electrodes are positioned to be equally spaced apart in order, alignment and parallel with each other, wherein said top ends of the respective left and right electrodes are electrically connected in parallel by a first lead wire serving as a first electrical pole, said top end of said middle electrode is connected by a second lead wire serving as a second electrical pole, said measurement sensor is positioned into an oil system of a machine, wherein said sensing capacitive sensor is immersed into an oil that is dry and disposed into said oil system;
   b. a reference sensor comprising a referencing capacitive sensor that is identical to said sensing capacitive sensor, said referencing capacitive sensor is immersed into a reference oil that is positioned inside of a sealed container of said reference sensor, said reference sensor is positioned in a common temperature environment with said oil of said oil system;
   c. an alternating current (AC) analyzing device is connected to said sensing and referencing capacitive sensors, wherein said AC analyzing device applies an AC voltage at a frequency to said sensors from a first measurement to thereby detect first measured electrical properties of the respective sensing and referencing capacitive sensors;
   d. said first measured electrical properties are combined to obtain a first measured temperature compensated electrical property of said sensing capacitive sensor, which represents a first measured temperature compensated electrical property of said oil;
   e. a profile of predicted temperature compensated electrical properties of said oil is obtained so that said first measured temperature compensated electrical property of said oil is compared with a first predicted temperature compensated electrical property of said oil according to a first actual usage of said oil from said profile of said predicted properties;
   f. a first predicted remaining usage of said oil is determined according to said first actual usage of said oil, and a second measured temperature compensated electrical property of said oil is obtained according to said first actual usage of said oil from a second measurement to thereby obtain a second measured remaining usage of said oil;
   g. a normal deterioration of said oil is determined which occurs in the absence of water if said second measured remaining usage is similar to said first predicated remaining usage, and said second measured remaining usage is confirmed to represent a remaining actual usage of said oil;
   h. an abnormal deterioration of said oil is determined which occurs in the presence of water if said second measured remaining usage is less than said first predicated remaining usage; and
   i. a top level of said oil is determined to reduce to a top level of a predetermined threshold amount of said oil if said second measured remaining usage is larger than said first predicted remaining usage.

2. The sensor as claimed in claim 1 at step c, wherein said electrical property is selected from the group consisting of impedance, resistance, reactance, phase angle, voltage and current.

3. The sensor as claimed in claim 1, further comprising spacers of insulating materials that are positioned between two adjacent plated electrodes, and said electrodes are affixed by additional insulating means to thereby keep a fixed gap between said two adjacent plated electrodes.

4. The sensor as claimed in claim 1, said sensing capacitive sensor further includes a total of an odd number of identical plated electrodes that are positioned equally spaced apart, in order, alignment and parallel with each other, wherein odd numbered plated electrodes of said total electrodes are connected in parallel by a first lead wire serving as a first electrical pole to thereby form a first group of integrated electrodes, and even numbered electrodes are connected in parallel by a second lead wire serving as a second electrical pole to thereby form a second group of integrated electrodes.

5. The sensor as claimed in claim 1, wherein said sensing capacitive sensor is positioned to align with said top level of said predetermined threshold amount of said oil of said machine, wherein said oil is a lubricating oil, and said machine is an internal combustion engine.

6. The sensor as claimed in claim 1, wherein said reference oil is selected from the group consisting of an unused oil, a partially spent oil and spent oil, and said reference oil has a similar thermal property as compared with a thermal property of said oil.

7. The sensor as claimed in claim 1, further comprising:
   a. a normal deterioration of said oil is determined which occurs in the absence of water if said second measured temperature compensated electrical property of said oil is similar to said first predicated temperature compensated electrical property of said oil;
   b. an abnormal deterioration of said oil is determined which occurs in the presence of water if said second measured temperature compensated electrical property of said oil is less than said first predicated temperature compensated electrical property of said oil; and
   c. a top level of said oil is determined to reduce to said top level of said predetermined threshold amount of said oil if said second measured temperature compensated electrical property of said oil is larger than said first predicated temperature compensated electrical property of said oil.

8. The sensor as claimed in claim 1 at step f, further comprising:
   a. a second measured remaining actual usage of said oil is $\Delta U_{M2}=(U_S-U_{M2})$, wherein said $U_{M2}$ is a second measured actual usage of said oil which is corresponding with said second measured temperature compensated electrical property, said $U_S$ is an actual usage of said oil which is spent;
   b. a first predicted remaining actual usage of said oil is $\Delta U_P=U_S-U_P$, wherein said $U_P$ is a first predicted actual usage of said oil which is corresponding with said first predicted property;
   c. a normal deterioration of said oil is determined which occurs in the absence of water if said second measured remaining actual usage $\Delta U_{M2}$, is similar to said first predicted remaining actual usage $\Delta U_P$, and confirming said second measured remaining actual usage;
   d. an abnormal deterioration of said oil is determined which occurs in the presence of water if said second measured remaining actual usage $\Delta U_{M2}$ is less than said first predicted remaining actual usage $\Delta U_P$; and
   e. a top level of said oil is determined to reduce to said top level of said predetermined threshold amount of said oil if said second measured remaining actual usage $\Delta U_{M2}$ is larger than said first predicted remaining actual usage $\Delta U_P$.

9. The sensor as claimed in claim 1 at step f, further comprising:
   a. a second measured temperature compensated electrical property of said sensing capacitive sensor according to a second actual usage of said oil is obtained from a second measurement to thereby represent a second measured temperature compensated electrical property of said oil according to said second actual usage of said oil, from which further to obtain a second measured remaining usage ratio and second measured remaining usage of said oil according to said second actual usage of said oil, a second predicted temperature compensated electrical property of said oil is obtained from said profile of said predicted temperature compensated electrical properties according to said second actual usage of said oil, from which further to obtain a second predicted remaining usage ratio and second predicted remaining usage of said oil according to said second actual usage of said oil;
   b. a top level of said oil is determined to reduce to said top level of said predetermined threshold amount of said oil if said second measured remaining usage of said oil is larger than said second predicted remaining usage of said oil;
   c. a top level of said oil is determined to reduce to said top level of said predetermined threshold amount of said oil if said second measured temperature compensated electrical property differs from said second predicted temperature compensated electrical property wherein said difference indicates less deterioration of said oil than deterioration predicted by said second predicted temperature compensated electrical property;
   d. a presence of water in said oil is determined if said first and second measured temperature compensated electrical properties of said oil according to the respective first and second actual usages of said oil have a rate of change of deterioration of said oil which differs from a rate of change of deterioration predicted by said first and second predicted temperature compensated electrical properties of said oil according to the respective first and second actual usages of said oil, wherein said difference indicates extra deterioration of said oil than deterioration predicted by said first and second predicted temperature compensated electrical properties;
   e. a likely presence of water in said oil is determined if said second measured temperature compensated electrical property of said oil having a value which exceeds a predetermined extreme value of said predicted temperature compensated electrical property profile, wherein said predetermined extreme value is exceeded at a said second actual usage which is earlier than an actual usage predicted by said predicted temperature compensated electrical property profile; and
   f. a second calibration means for counting elapsed actual usages.

10. The sensor as claimed in claim 1 at step f, further comprising:
    a. a second measured temperature compensated electrical property of said sensing capacitive sensor according to a second actual usage of said oil is obtained from a second measurement to thereby represent a second measured temperature compensated electrical property of said oil according to said second actual usage of said oil, from which further to obtain a second measured remaining actual usage of said oil, a second predicted temperature compensated electrical property of said oil is obtained from said profile of said predicted temperature compensated electrical properties according to said second actual usage of said oil, from which further to obtained a second predicted remaining actual usage of said oil;
    b. a top level of said oil is determined to reduce to said top level of said predetermined threshold amount of said oil if said second measured remaining actual usage of said oil is larger than said second predicted remaining actual usage of said oil; and
    c. a second calibration means for counting elapsed actual usages.

11. A sensor for detecting oil deterioration and oil level, comprising:
    a. a measurement sensor comprising a sensing capacitive sensor that includes left, middle and right identical upward plated spatial electrodes having the respective top and bottom ends, said electrodes are positioned to be equally spaced apart in order, alignment and parallel with each other, wherein said top ends of the respective left and right electrodes are electrically connected in parallel by a first lead wire serving as a first electrical pole, said top end of said middle electrode is connected by a second lead wire serving as a second electrical pole, said measurement sensor is positioned into an oil system of a machine, wherein said sensing capacitive sensor is immersed into an oil that is dry and disposed into said oil system;
    b. an alternating current (AC) analyzing device is connected to said sensing capacitive sensor, wherein said AC analyzing device applies an AC voltage at a frequency to said sensor from a first measurement to thereby detect a first measured temperature compensated electrical property of said sensing capacitive sensor that represents a first measured temperature compensated electrical property of said oil;
    c. a profile of predicted temperature compensated electrical properties of said oil is obtained so that said first measured temperature compensated electrical property of said oil is compared with a first predicted temperature compensated electrical property of said oil according to a first actual usage of said oil from said profile of said predicted properties;

d. a first predicted remaining usage of said oil is determined according to said first actual usage of said oil, and a second measured temperature compensated electrical property of said oil is obtained according to said first actual usage of said oil from a second measurement to thereby obtain a second measured remaining usage of said oil;

e. a normal deterioration of said oil is determined which occurs in the absence of water if said second measured remaining usage is similar to said first predicated remaining usage, and said second measured remaining usage is confirmed to represent a remaining actual usage of said oil;

f. an abnormal deterioration of said oil is determined which occurs in the presence of water if said second measured remaining usage is less than said first predicated remaining usage; and g. a top level of said oil is determined to reduce to a top level of a predetermined threshold amount of said oil if said second measured remaining usage is larger than said first predicted remaining usage.

12. The sensor as claimed in claim 11 at step b, wherein said electrical property is selected from the group consisting of impedance, resistance, reactance, phase angle, voltage and current.

13. The sensor as claimed in claim 11, further comprising spacers of insulating materials that are positioned between two adjacent plated electrodes, and said electrodes are affixed by additional insulating means to thereby keep a fixed gap between said two adjacent plated electrodes.

14. The sensor as claimed in claim 11, said sensing capacitive sensor further includes a total of an odd number of identical plated electrodes that are positioned equally spaced apart, in order, alignment and parallel with each other, wherein odd numbered plated electrodes of said total electrodes are connected in parallel by a first lead wire serving as a first electrical pole to thereby form a first group of integrated electrodes, and even numbered electrodes are connected in parallel by a second lead wire serving as a second electrical pole to thereby form a second group of integrated electrodes.

15. The sensor as claimed in claim 11, wherein said sensing capacitive sensor is positioned to align with said top level of said predetermined threshold amount of said oil of said machine, wherein said oil is a lubricating oil, and said machine is an internal combustion engine.

16. The sensor as claimed in claim 11, further comprising:
a. a normal deterioration of said oil is determined which occurs in the absence of water if said second measured temperature compensated electrical property of said oil is similar to said first predicated temperature compensated electrical property of said oil;
b. an abnormal deterioration of said oil is determined which occurs in the presence of water if said second measured temperature compensated electrical property of said oil is less than said first predicated temperature compensated electrical property of said oil; and
c. a top level of said oil is determined to reduce to said top level of said predetermined threshold amount of said oil if said second measured temperature compensated electrical property of said oil is larger than said first predicated temperature compensated electrical property of said oil.

17. The sensor as claimed in claim 11 at step d, further comprising:
a. a second measured remaining actual usage of said oil is $\Delta U_{M2}=(U_S-U_{M2})$, wherein said $U_{M2}$ is a second measured actual usage of said oil which is corresponding with said second measured temperature compensated electrical property, said $U_S$ is an actual usage of said oil which is spent;
b. a first predicted remaining actual usage of said oil is $\Delta U_P=U_S-U_P$, wherein said $U_P$ is a first predicted actual usage of said oil which is corresponding with said first predicted property;
c. a normal deterioration of said oil is determined which occurs in the absence of water if said second measured remaining actual usage $\Delta U_{M2}$ is similar to said first predicted remaining actual usage $\Delta U_P$, and confirming said second measured remaining actual usage;
d. an abnormal deterioration of said oil is determined which occurs in the presence of water if said second measured remaining actual usage $\Delta U_{M2}$ is less than said first predicted remaining actual usage $\Delta U_P$; and
e. a top level of said oil is determined to reduce to said top level of said predetermined threshold amount of said oil if said second measured remaining actual usage $\Delta U_{M2}$ is larger than said first predicted remaining actual usage $\Delta U_P$.

18. The sensor as claimed in claim 11 at step d, further comprising:
a. a second measured temperature compensated electrical property of said sensing capacitive sensor according to a second actual usage of said oil is obtained from a second measurement to thereby represent a second measured temperature compensated electrical property of said oil according to said second actual usage of said oil, from which further to obtain a second measured remaining usage ratio and second measured remaining usage of said oil according to said second actual usage of said oil, a second predicted temperature compensated electrical property of said oil is obtained from said profile of said predicted temperature compensated electrical properties according to said second actual usage of said oil, from which further to obtain a second predicted remaining usage ratio and second predicted remaining usage of said oil according to said second actual usage of said oil;
b. a top level of said oil is determined to reduce to said top level of said predetermined threshold amount of said oil if said second measured remaining usage of said oil is larger than said second predicted remaining usage of said oil;
c. a top level of said oil is determined to reduce to said top level of said predetermined threshold amount of said oil if said second measured temperature compensated electrical property differs from said second predicted temperature compensated electrical property wherein said difference indicates less deterioration of said oil than deterioration predicted by said second predicted temperature compensated electrical property;
d. a likely presence of water in said oil is determined if said first and second measured temperature compensated electrical properties of said oil according to the respective first and second actual usages of said oil have a rate of change of deterioration of said oil which differs from a rate of change of deterioration predicted by said first and second predicted temperature compensated electrical properties of said oil according to the respective first and second actual usages of said oil, wherein said difference indicates extra deterioration of said oil than deterioration predicted by said first and second predicted temperature compensated electrical properties;

e. a presence of water in said oil is determined if said second measured temperature compensated electrical property of said oil according to said second actual usage of said oil having a value which exceeds a predetermined extreme value of said predicted temperature compensated electrical property profile, wherein said predetermined extreme value is exceeded at said second actual usage which is earlier than an actual usage predicted by said predicted temperature compensated electrical property profile; and f. a second calibration means for counting elapsed actual usages.

19. The sensor as claimed in claim 11 at step d, further comprising:

a. a second measured temperature compensated electrical property of said sensing capacitive sensor according to a second actual usage of said oil is obtained from a second measurement to thereby represent a second measured temperature compensated electrical property of said oil according to said second actual usage of said oil, from which further to obtain a second measured remaining actual usage of said oil, a second predicted temperature compensated electrical property of said oil is obtained from said profile of said predicted temperature compensated electrical properties according to said second actual usage of said oil, from which further to obtained a second predicted remaining actual usage of said oil;

b. a top level of said oil is determined to reduce to said top level of said predetermined threshold amount of said oil if said second measured remaining actual usage of said oil is larger than said second predicted remaining actual usage of said oil; and c. a second calibration means for counting elapsed actual usages.

20. A sensor for detecting oil deterioration and oil level, comprising:

a. identical first and second measurement sensors comprising the respective identical first and second sensing capacitive sensors, wherein each of said sensing capacitive sensors includes left, middle and right identical upward plated electrodes having the respective top and bottom ends, which are positioned to be equally spaced apart in order, alignment and parallel with each other, wherein said top ends of the respective left and right electrodes are electrically connected in parallel by a first lead wire serving as a first electrical pole, said top end of said middle electrode is connected by a second lead wire serving as a second electrical pole, said first measurement sensor is positioned into a first location of an oil system of a machine wherein said first sensing capacitive sensor is immersed into a first oil that is dry and disposed into said first location of said oil system, said second measurement sensor is positioned into a second location of said oil system of said machine, wherein said second capacitive sensor is immersed into a second oil that is dry and disposed into said second location, said first oil and second oil are identical and have a same temperature;

b. a reference sensor comprising a referencing capacitive sensor that is identical to said first sensing capacitive sensor, said referencing capacitive sensor is immersed into a reference oil that is positioned inside of a sealed container of said reference sensor, said reference sensor is positioned in a common temperature environment with said first oil and second oil of said oil system c. an alternating current (AC) analyzing device is connected to said referencing, first and second sensing capacitive sensors, wherein said AC analyzing device applies an AC voltage at a frequency to said sensors from a first measurement to thereby detect first measured electrical properties of the respective first sensing, second sensing and referencing capacitive sensors;

d. said first measured electrical properties of the respective first sensing and referencing capacitive sensors are combined to obtain a first measured temperature compensated electrical property of said first sensing capacitive sensor that represents a first measured temperature compensated electrical property of said first oil, said first measured electrical properties of the respective second sensing and referencing capacitive sensors are combined to obtain a first measured temperature compensated electrical property of said second sensing capacitive sensor that represents a first measured temperature compensated electrical property of said second oil;

e. a first predicted temperature compensated electrical property of said first oil is compared with said first measured temperature compensated electrical property of said first oil positioned in said first location from a profile of predicted temperature compensated electrical properties of said first oil to thereby determine a first predicted remaining usage of said first oil, which correlates to a first actual usage of said first oil from said profile of said predicted properties;

f. second measured temperature compensated electrical properties of the respective first oil and second oil positioned in the respective first and second locations are obtained according to said first actual usage of said first oil from a second measurement to thereby obtain second measured remaining usages of the respective first oil and second oil;

g. an even distribution of an oil normal deterioration is determined which occurs in the absence of water if said second measured remaining usages of the respective first oil and second oil are similar to said first predicated remaining usage of said first oil, and one of said second measured remaining usages is confirmed to represent an oil remaining actual usage; and h. an uneven distribution of deterioration of the respective first oil and second oil is determined if said second measured remaining usages of the respective first oil and second oil are different from each other, as compared with said first predicated remaining usage of said first oil.

21. The sensor as claimed in claim 20 at step c, wherein said electrical property is selected from the group consisting of impedance, resistance, reactance, phase angle, voltage and current.

22. The sensor as claimed in claim 20, further comprising spacers of insulating materials that are positioned between two adjacent plated electrodes, and said electrodes are affixed by additional insulating means to thereby maintain a fixed gap between said two adjacent plated electrodes.

23. The sensor as claimed in claim 20, said first sensing capacitive sensor further includes a total of an odd number of identical plated electrodes that are positioned equally spaced apart, in order, alignment and parallel with each other, wherein odd numbered plated electrodes of said total electrodes are connected in parallel by a first lead wire serving as a first electrical pole to thereby form a first group of integrated electrodes, and even numbered electrodes are connected in parallel by a second lead wire serving as a second electrical pole to thereby form a second group of integrated electrodes.

24. The sensor as claimed in claim 20, wherein said reference oil is selected from the group consisting of an unused oil, a partially spent oil and spent oil, and said reference oil has a similar thermal property as compared with a thermal property of said first oil, and said first oil is a lubricating oil, and said machine is an internal combustion engine.

* * * * *